(12) United States Patent
Bennett

(10) Patent No.: US 8,845,686 B2
(45) Date of Patent: Sep. 30, 2014

(54) SURGICAL SUTURE SYSTEM

(75) Inventor: William F. Bennett, Sarasota, FL (US)

(73) Assignee: Ziptek LLC., Sarosota, FL (US)

( * ) Notice: Subject to any disclaimer, the term of this patent is extended or adjusted under 35 U.S.C. 154(b) by 151 days.

(21) Appl. No.: 13/281,963

(22) Filed: Oct. 26, 2011

(65) Prior Publication Data

US 2012/0101526 A1 Apr. 26, 2012

Related U.S. Application Data

(63) Continuation-in-part of application No. 12/912,313, filed on Oct. 26, 2010.

(51) Int. Cl.
*A61B 17/04* (2006.01)
*A61B 17/06* (2006.01)
(52) U.S. Cl.
CPC ..... *A61B 17/0401* (2013.01); *A61B 2017/0441* (2013.01); *A61B 2017/0427* (2013.01); *A61B 2017/045* (2013.01); *A61B 2017/0438* (2013.01); *A61B 2017/06176* (2013.01); *A61B 2017/0404* (2013.01); *A61B 2017/0462* (2013.01); *A61B 2017/044* (2013.01); *A61B 17/0466* (2013.01); *A61B 2017/0456* (2013.01); *A61B 17/06166* (2013.01)
USPC ........................................ 606/232
(58) Field of Classification Search
CPC ........... A61B 17/0401; A61B 17/0485; A61B 2017/0461; A61B 2017/0462; A61B 2017/06176; A61B 17/0466; A61B 17/06166; A61B 2017/0404; A61B 2017/0427; A61B 2017/0438; A61B 2017/044; A61B 2017/045; A61B 2017/0456
USPC ............... 606/228–232, 72, 73, 300, 301, 74, 606/103, 153; 24/30.5, 129 R, 130, 129 B, 24/129 W; 411/531, 539, 540, 545; 206/523
See application file for complete search history.

(56) References Cited

U.S. PATENT DOCUMENTS

| | | | | |
|---|---|---|---|---|
| 4,741,330 A | * | 5/1988 | Hayhurst | 606/144 |
| 4,898,156 A | | 2/1990 | Gatturna et al. | |
| 5,370,661 A | | 12/1994 | Branch | |
| 5,413,585 A | | 5/1995 | Pagedas | |
| 5,725,556 A | * | 3/1998 | Moser et al. | 606/232 |
| 5,938,686 A | | 8/1999 | Benderev et al. | |

(Continued)

FOREIGN PATENT DOCUMENTS

WO WO 2012/058301 5/2012

OTHER PUBLICATIONS

U.S. Appl. No. 13/281,963, filed Oct. 26, 2011, Bennett.
U.S. Appl. No. 13/664,717, filed Oct. 31, 2012, Bennett.

*Primary Examiner* — Julian W Woo
(74) *Attorney, Agent, or Firm* — Frijouf, Rust & Pyle P.A.

(57) ABSTRACT

A surgical suture system, suture, and tissue engaging member for tissue repair and reattachment of torn tissue to a tissue substrate, medical prosthesis or medical implant. The system includes the elongated flexible suture member having a plurality of longitudinally spaced protuberances along a length thereof and one or a plurality of the tissue engaging members each of which include two closely spaced apart locking apertures sized and configured to receive one of the suture members passed therethrough or a unique single locking aperture to allow longitudinal tensioning and/or restraining movement of the suture member in only one direction through the locking apertures for suture member tightening.

9 Claims, 27 Drawing Sheets

(56) References Cited

U.S. PATENT DOCUMENTS

| | | |
|---|---|---|
| 6,013,083 A | 1/2000 | Bennett |
| 6,015,410 A | 1/2000 | Tormala et al. |
| 6,015,428 A * | 1/2000 | Pagedas ............... 606/232 |
| 6,117,162 A | 9/2000 | Schmieding et al. |
| 6,206,886 B1 | 3/2001 | Bennett |
| 6,214,031 B1 | 4/2001 | Schmieding et al. |
| 6,293,961 B2 | 9/2001 | Schwartz et al. |
| 6,491,714 B1 | 12/2002 | Bennett |
| 6,499,599 B1 * | 12/2002 | Hopkins et al. ............ 206/523 |
| 6,533,802 B2 | 3/2003 | Bojarski et al. |
| 7,303,577 B1 | 12/2007 | Dean |
| 7,530,990 B2 | 5/2009 | Perriello et al. |
| 7,585,311 B2 | 9/2009 | Green et al. |
| 7,615,061 B2 | 11/2009 | White et al. |
| 7,637,926 B2 | 12/2009 | Foerster et al. |
| 7,658,750 B2 | 2/2010 | Li |
| 7,658,751 B2 | 2/2010 | Stone et al. |
| 7,682,374 B2 | 3/2010 | Foerster et al. |
| 7,686,838 B2 | 3/2010 | Wolf et al. |
| 7,695,494 B2 | 4/2010 | Foerster |
| 2001/0025181 A1 * | 9/2001 | Freedlan ............... 606/73 |
| 2002/0004668 A1 | 1/2002 | Bartlett |
| 2002/0004669 A1 | 1/2002 | Bartlett |
| 2002/0007196 A1 | 1/2002 | Bartlett |
| 2005/0251209 A1 * | 11/2005 | Saadat et al. ............ 606/232 |
| 2006/0106422 A1 | 5/2006 | Del Rio et al. |
| 2006/0106423 A1 | 5/2006 | Weisel et al. |
| 2007/0156151 A1 | 7/2007 | Guan et al. |
| 2007/0282375 A1 | 12/2007 | Hindrichs et al. |
| 2008/0082113 A1 | 4/2008 | Bishop et al. |
| 2012/0101526 A1 | 4/2012 | Bennett |

* cited by examiner

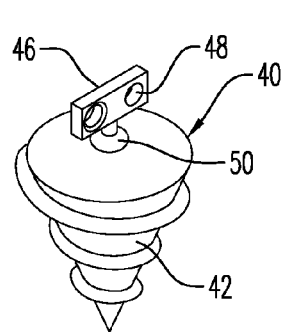
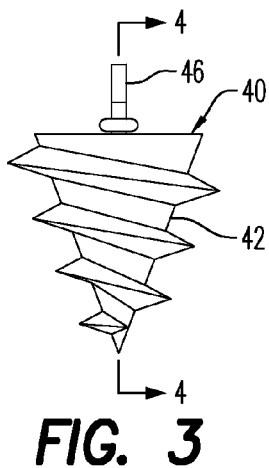
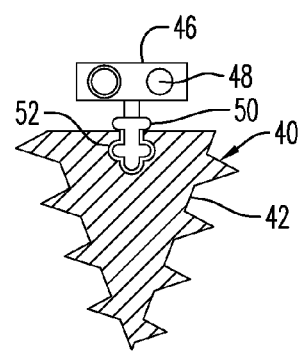
FIG. 2    FIG. 3    FIG. 4
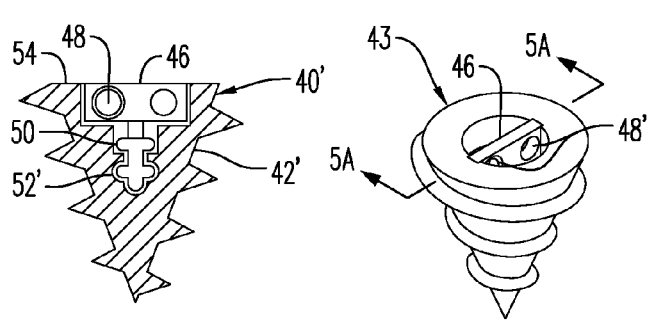
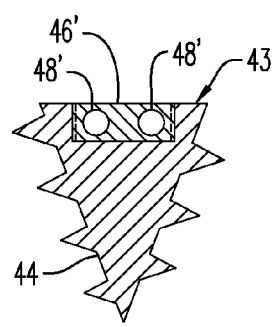
FIG. 4A    FIG. 5    FIG. 5A

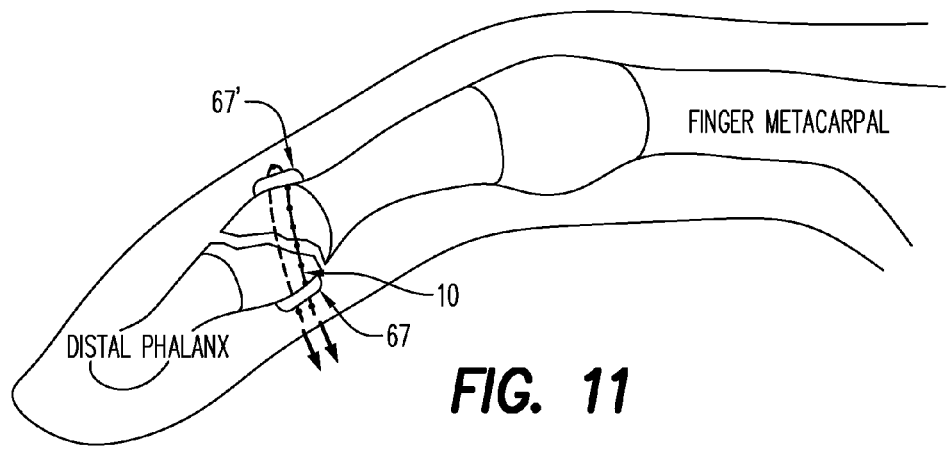
FIG. 11
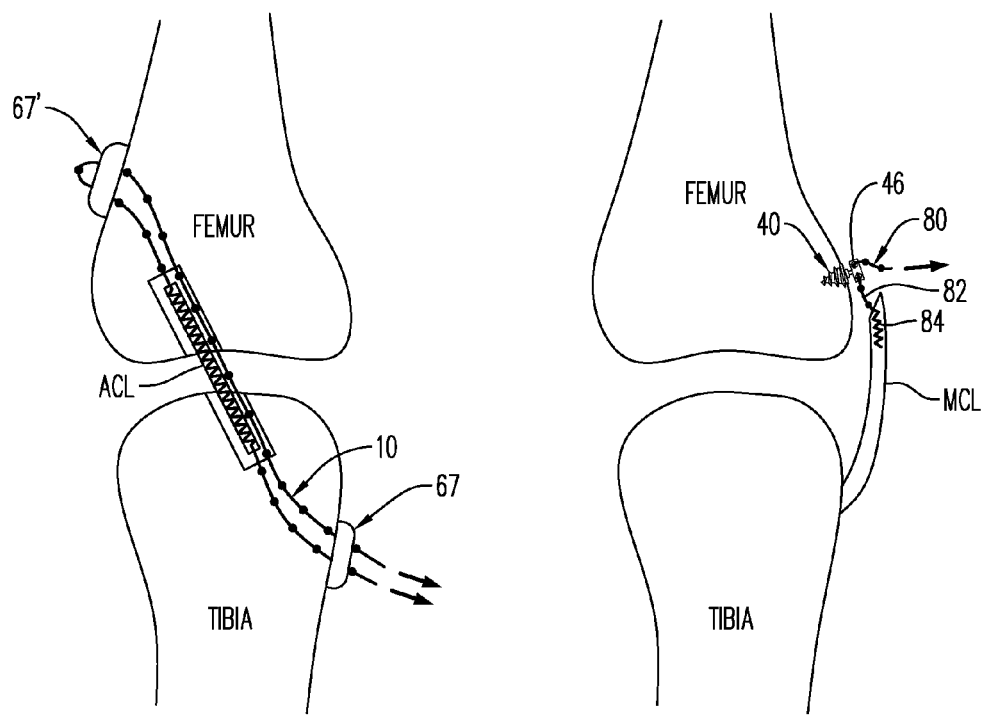
FIG. 12　　　FIG. 13

HIP LABRAL REPAIR

DISTAL BICEPS REPAIR

ANKLE SYNDESMOTIC DISRUPTION

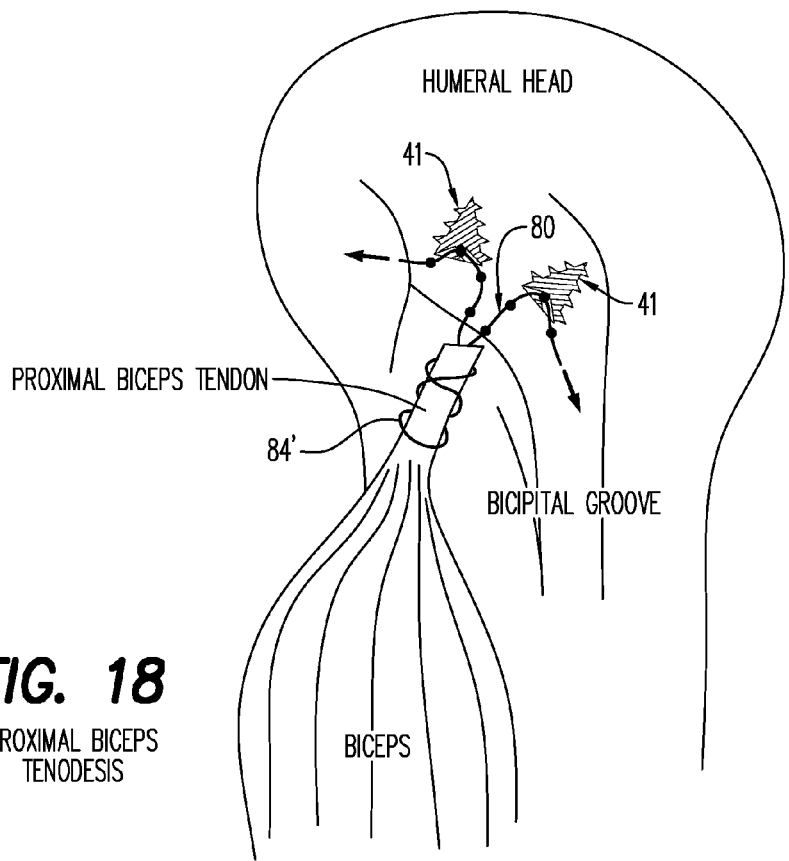
FIG. 18
PROXIMAL BICEPS
TENODESIS
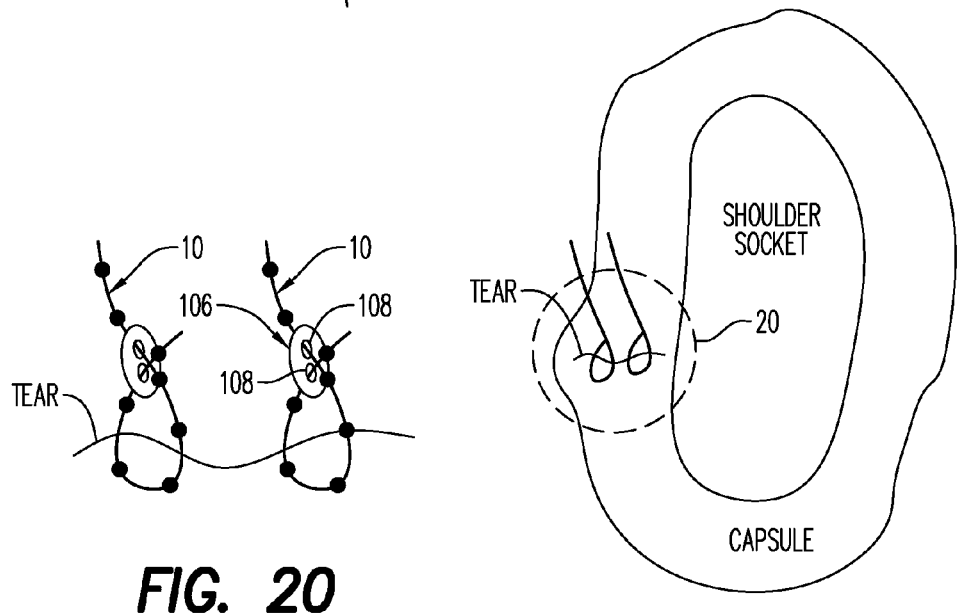
FIG. 20
FIG. 19
JOINT CAPSULE REPAIR WITH
FREE CAPTURE WITHOUT ANCHOR

SHOULDER LABRAL REPAIR

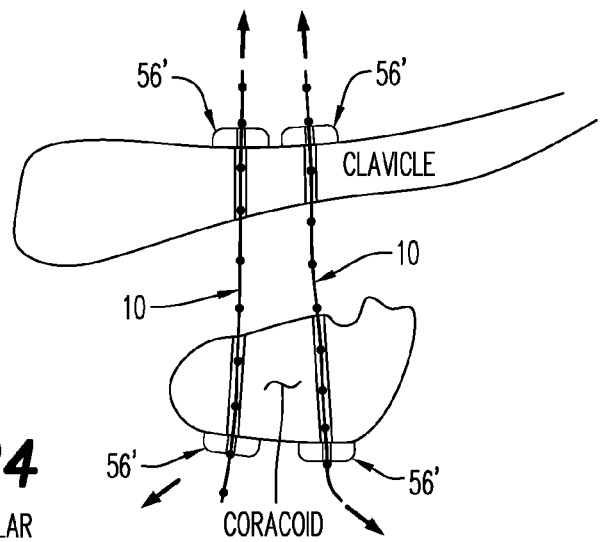
FIG. 24
CORACOCLAVICULAR
LIGAMENT REPAIR
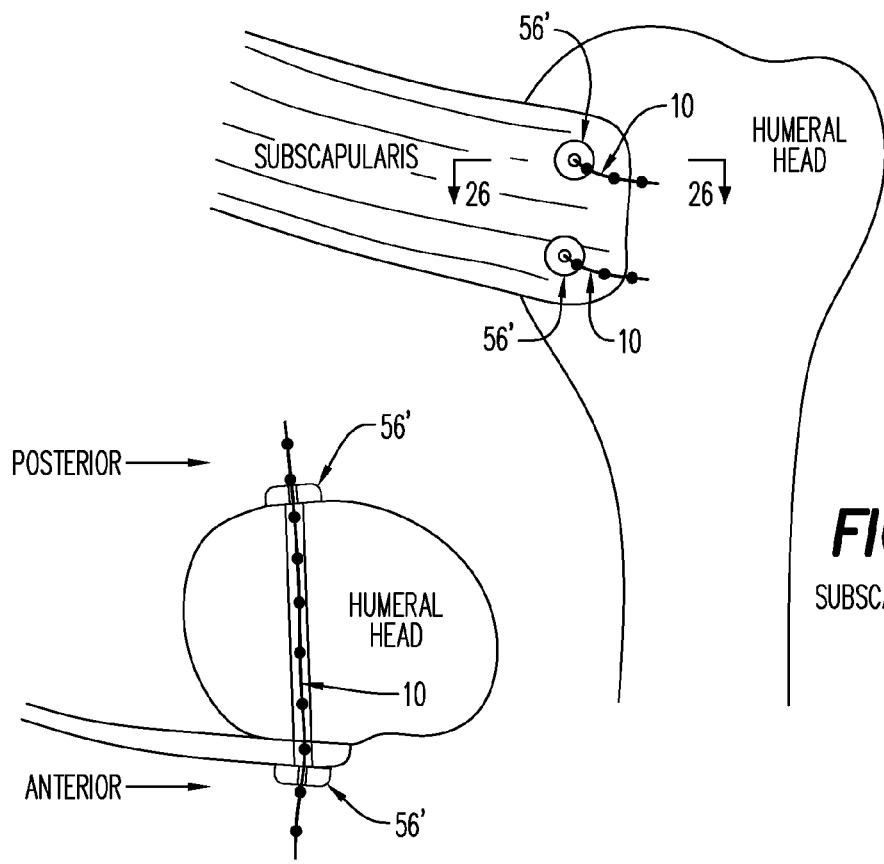
FIG. 25
SUBSCAPULARIS REPAIR
FIG. 26

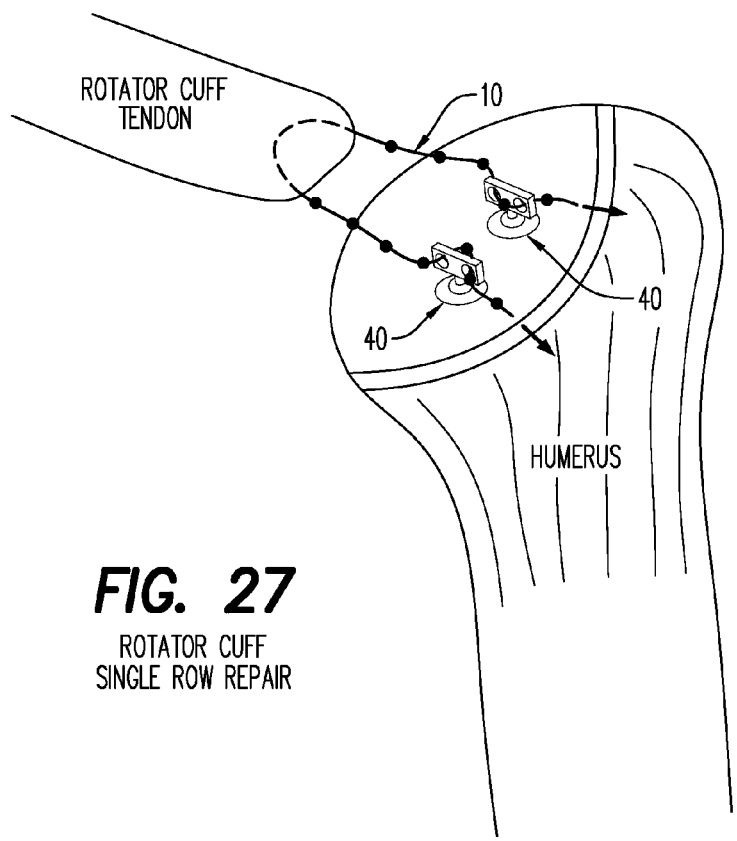
FIG. 27
ROTATOR CUFF
SINGLE ROW REPAIR
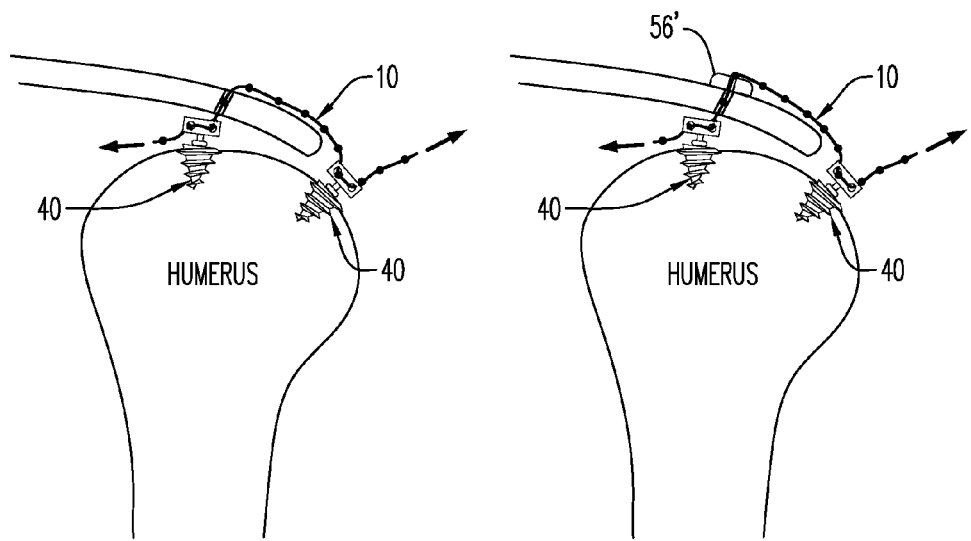
FIG. 28    FIG. 29
DOUBLE ROW
REPAIR

MENISCAL REPAIR
SAGITTAL VIEW

MENISCAL REPAIR
FIXED OR WITH
INTERFACE

MENISCAL REPAIR
MULTIPLE REPAIRS

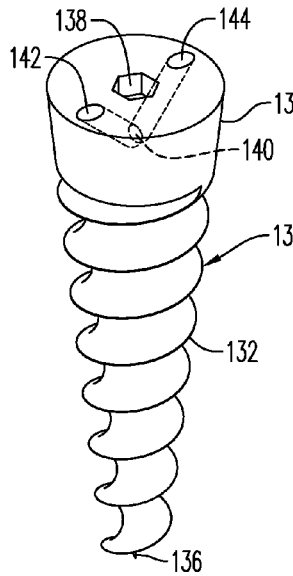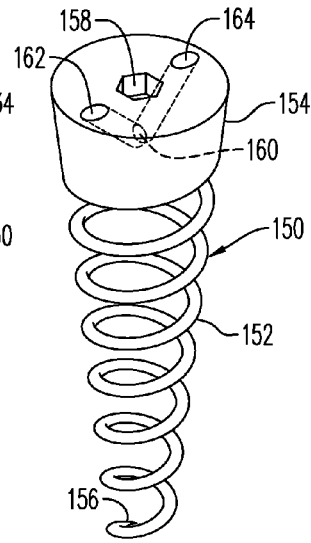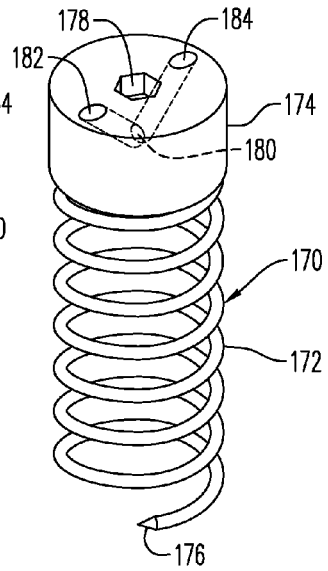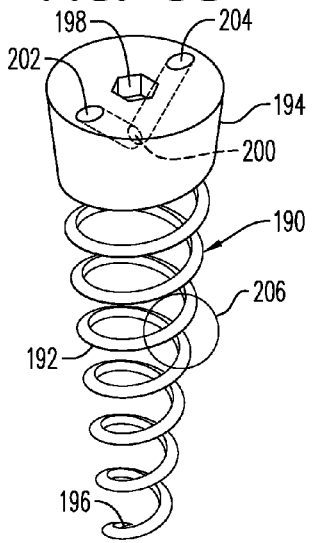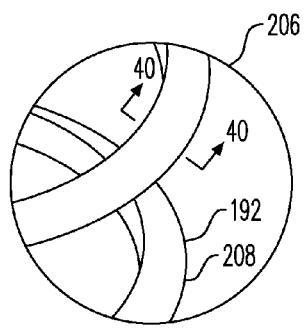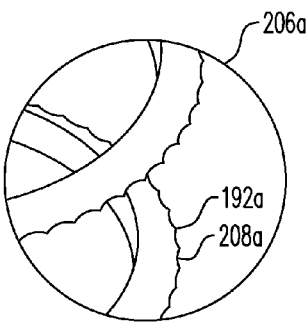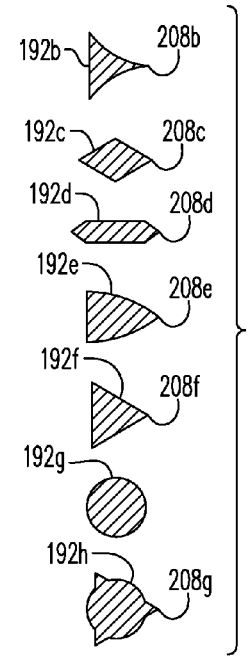

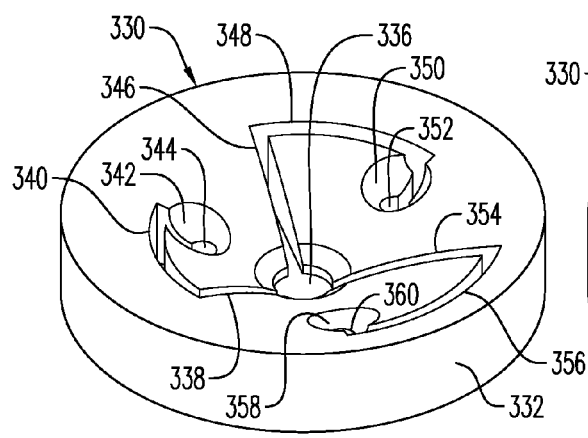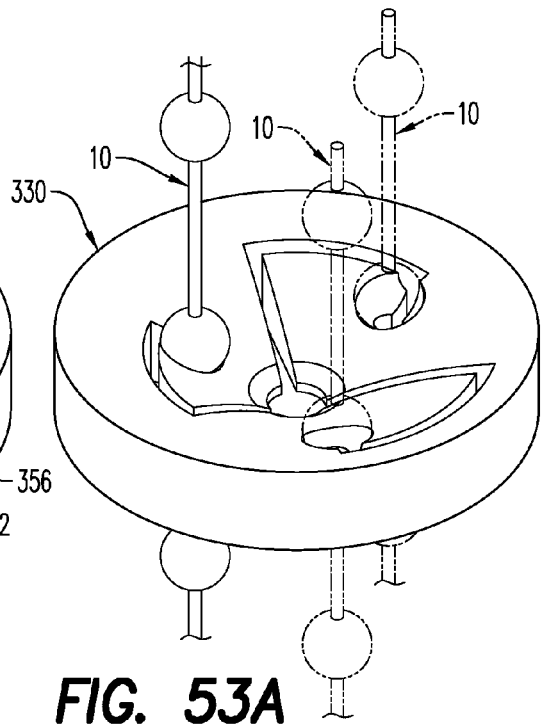
FIG. 53
FIG. 53A
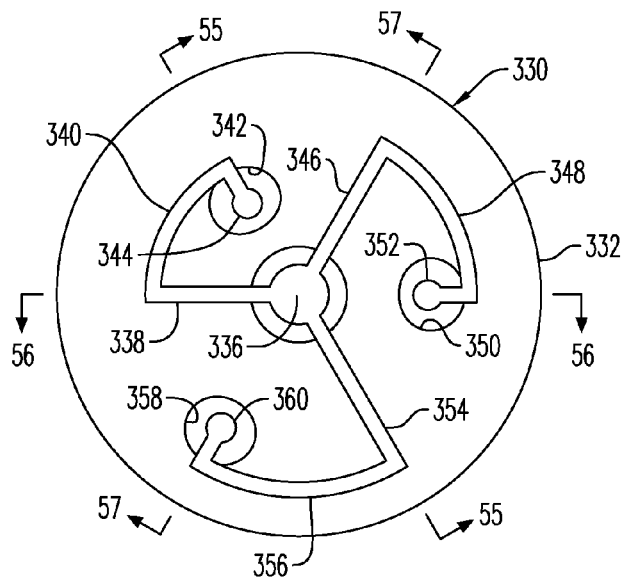
FIG. 54

SURGICAL SUTURE SYSTEM

CROSS-REFERENCE TO RELATED APPLICATIONS

This application is a continuation-in-part of application Ser. No. 12/912,313, filed Oct. 26, 2010.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to surgical apparatus and methods for repair of torn tissue, and more particularly to an apparatus and method for arthroscopic and other surgical repair of torn tissue and tissue reattachment by providing a system for suturing and anchoring the torn tissue, together, against other tissue substrates, or for attaching tissue to medical implants.

2. Description of Related Art

The rotator cuff is composed of four tendons that blend together to help stabilize and move the shoulder. When a tear occurs in the rotator cuff of the shoulder, it is often necessary to reattach the torn tendon or tendons to the bone of the humeral head. In a common prior art rotator cuff reattachment technique, the torn cuff is punctured by a punch, and prethreaded suture anchor screws (soft tissue fasteners) are drilled into the head of the humerus bone and the sutures threaded through the anchor screws are passed through the cuff in a difficult procedure using suture relay devices to pass the sutures through the tissue. After the suture strands are passed through the tissue, they are knotted and tied together to secure the reattached rotator cuff to the humerus head. Other types of prior art suture anchors are conically shaped members that are pressed into holes drilled into the bone and engage the cancellous mass surrounding the drilled hole.

A major problem with the above described suture anchoring technique is that the threaded suture anchor screws or conically shaped anchors are threadedly or otherwise secured to the cancellous bone mass beneath the near cortex of the head of the humerus, and depend on this cancellous mass for fixation. It is well known that the cancellous bone mass is susceptible to osteopenic changes (diminished amount of bone tissue).

As a result, the pull-out strength of suture anchors which are dependent on the cancellous bone mass beneath the cortex of the bone is subject to becoming diminished with time, and the anchors will tend to loosen, thereby possibly requiring a second operation to remove the loosened suture anchor.

Another problem with the conventional technique is that, in most cases, the sutures are not passed through the tissue when the anchor is set, and thus a difficult procedural step is required using devices such as punches and suture relays to pass and tie the sutures through the torn tissue.

Additionally, many anchor/suture devices require knots to be tied which is difficult with minimally invasive surgery and having a "knotless" solution is an advantage.

In my prior U.S. Pat. No. 6,491,714, an apparatus and method for arthroscopic repair of torn tissue such as a rotator cuff was taught wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool.

The deployment tool is passed through the inner cannula and a hole is drilled until the expandable wings clear the far end of the hole, a sufficient distance to allow the wings to expand to a diameter larger than the diameter of the drilled hole. The deployment tool, inner cannula, drill guide and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

Unlike conventional soft tissues anchors which are anchored in the cancellous bone mass beneath the near cortex of the bone, the '714 teaching in one embodiment provides a suture anchor which is engaged on the exterior of the far cortex of the bone and completely bypasses the cancellous bone mass. The cortex of the bone is much less susceptible to osteopenia than the cancellous interior of the bone. The sutures are passed through the tissue when the anchor is set, and thus the difficult procedural step and use of devices such as punches and suture relays to pass and tie the sutures through the torn tissue is eliminated.

Calibrated markings on the '714 deployment system allow for precise measurement of the far cortex and precise measurement of the depth of insertion and engagement of the anchor device on the far cortex, such that structures beyond the cortex are not violated, and the button hold-down feature eliminates the traditionally difficult arthroscopic tying techniques.

In another broader aspect of the '714 invention, the surgical apparatus includes any form of a tissue substrate anchor of a conventional well-known structure, an elongated suture member securable at its proximal end to the anchor, and a separate torn tissue retainer which lockably engages as desired along the length of the suture member. The suture member extending through the torn tissue from the anchor and the tissue substrate. The torn tissue retainer is movable along the length of the exposed portion of the suture member until it is tightly positioned against the torn tissue and automatically locked in that position by non-reversible lockable engagement with the suture member. A separate tissue gripping member formed preferably as a semi-flexible plate or disc having a substantially larger surface area than the tissue retainer is also provided for enhanced retention of the torn tissue in place against the outer surface of the tissue substrate.

Still another broad aspect of this '714 invention is directed to a surgical apparatus which includes an integrally formed tissue substrate anchor having an elongated suture member formed as a unit therewith. A separate disc-shaped retainer lockingly engages with the exposed distal end of the suture portion at any desired point along the suture interlocking portion. The tissue retainer is therefore moveable along the length of the exposed engaging members of the suture member for tightening the tissue layer against the tissue substrate. Utilized another way, a tear such as that found within a torn meniscus may be reconnected utilizing this embodiment of the invention.

Currently, soft-tissue fixation products that utilize "knot-less" technology and screws rely on an "interference-fit" for holding power between the screw and bone. In general, non-screw anchors have a pullout strength near 200 newtons, and screws can have upwards of 400 newtons of pullout strength.

The patent technology allows for the introduction of a revolutionary type of anchor for soft-tissue fixation to bone. Screws, as opposed to hook-type anchors, have the strongest pullout strength, "ZIP-TIE" patented technology will introduce its technology to the eyelet of screws. Specifically, it will attach one member of the suture to screws and this will allow for a ratcheting of the suture member through the suture capture or retainer or suture anchor, thereby creating a very strong construct.

The traditional repair of soft tissue requires sutures to be passed through the tissue. A knot is tied, which holds the torn tissue together, allowing for healing. Minimally invasive surgical techniques are being utilized through "button-hole" size incisions. Surgery is performed with instruments that pass through cannulas (like drainage culverts or pipes). Knots that would be utilized for this type of repair are tied and must be slid down through these cannulas. This technique can be difficult, result in adequate repair strength, provide for poor tissue approximation, for some surgeons, it may result in an inability to proceed with a minimally invasive approach secondary to the advanced technical difficulty, and finally, can add significant operative time to surgical procedures. USCO's patented technology is akin to a "cable or tie-wrap" that is utilized for holding electric wire or cables together. Based upon the patented interface, a "pipe-line" of products will be created using knot-less, self-locking interface as a technology development platform.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

The present disclosure is broadly directed to a surgical suture system for tissue repair and reattachment of torn tissue to a tissue substrate, medical prosthesis or medical implant. The system includes an elongated flexible suture member having a plurality of longitudinally spaced protuberances along a length thereof, and a plurality of tissue engaging members such as suture tissue restraints, anchors, and medical implants each including two spaced apart locking apertures sized to receive the suture member passed therethrough to allow longitudinal movement of the suture member in only one direction through the locking apertures for suture member tightening and retention.

It is therefore an object of this invention to provide a surgical suture system for tissue repair and reattachment of torn tissue together, to a tissue substrate or medical implant.

It is another object of this invention to provide a surgical suture system for repair of torn tissue such as a torn rotator cuff utilizing uniquely configured tissue engaging members, each of which include a double locking aperture arrangement of two closely spaced together locking apertures which receive the unique suture and cooperate for only one-way movement during tightening of the suture to bring torn tissue into a desired healing orientation.

A broad aspect of this disclosure provides for the reattachment of any torn or damaged tissue or artificial tissue to any form of tissue substrate or together by the use of a uniquely configured substrate anchor or tissue restraint having a double locking aperture arrangement for receiving a suture having spaced apart protuberances along the length of the suture. The suture tissue restraint or substrate anchor, or more broadly the tissue engaging member, is configured for movement of the suture itself through the pair of locking apertures in only one direction so that any tightening movement of the suture within the tissue engaging member is locked from reverse movement therebetween. A variety of spaced protuberance configurations along the length of the flexible elongated suture member are disclosed for this one-way locking movement engagement within one or more of the tissue engaging members each having the two spaced apart locking apertures formed therethrough to lockingly receive the suture members.

The following embodiments and aspects thereof are described and illustrated in conjunction with systems, tools and methods which are meant to be exemplary and illustrative and not limiting in scope. In various embodiments one or more of the above-described problems have been reduced or eliminated while other embodiments are directed to other improvements. In addition to the exemplary aspects and embodiments described above, further aspects and embodiments will become apparent by reference to the drawings and by study of the following descriptions.

BRIEF DESCRIPTION OF THE SEVERAL VIEWS OF THE DRAWING(S)

FIG. 2 is a perspective view of a suture anchor configured in accordance with this disclosure.

FIG. 3 is a side elevation view of FIG. 2.

FIG. 4 is a section view in the direction of arrows 4-4 in FIG. 3.

FIG. 4A is a section view similar to FIG. 4 depicting an alternate embodiment thereof.

FIG. 5 is a perspective view of another alternate embodiment of the suture anchor of FIG. 2.

FIG. 5A is a section view in the direction of arrows 5A-5A in FIG. 5.

Figure 10:
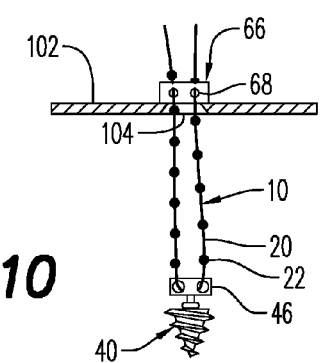

FIG. 10 is an elevation view of a typical installation arrangement of the elongated suture member 10 in locking engagement with a suture anchor 40 and a suture tissue restraint 66.

FIG. 11 is a simplified pictorial view of one aspect of the invention utilized to repair and restrain a broken distal phalanx of a finger metacarpal.

FIG. 12 is an elevation view utilizing another aspect of the present invention to repair torn ACL tissue of a knee joint.

FIG. 13 is an elevation view utilizing another aspect of the present invention to repair a torn MCL of a knee joint.

Figure 14:
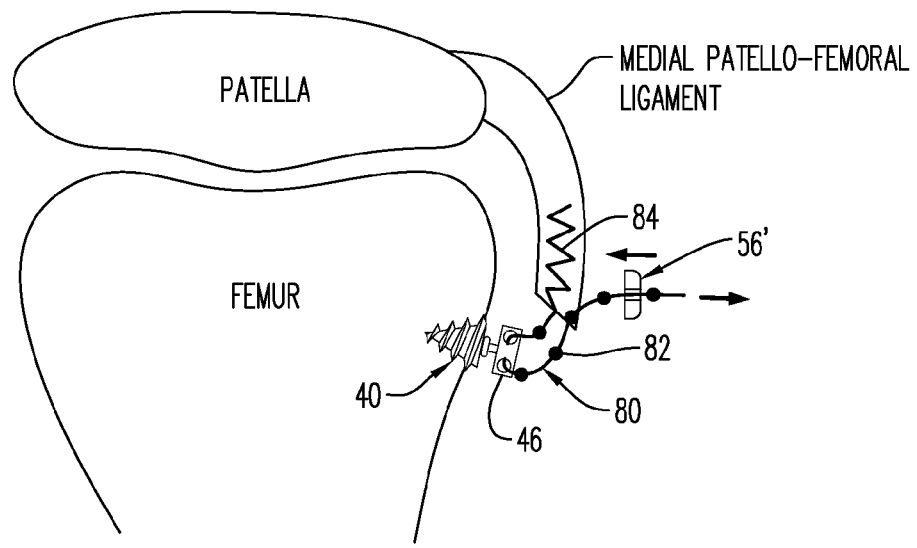

FIG. 14 is a side elevation view showing another aspect of the invention utilized to repair a torn medial patella-femoral ligament.

Figure 15:
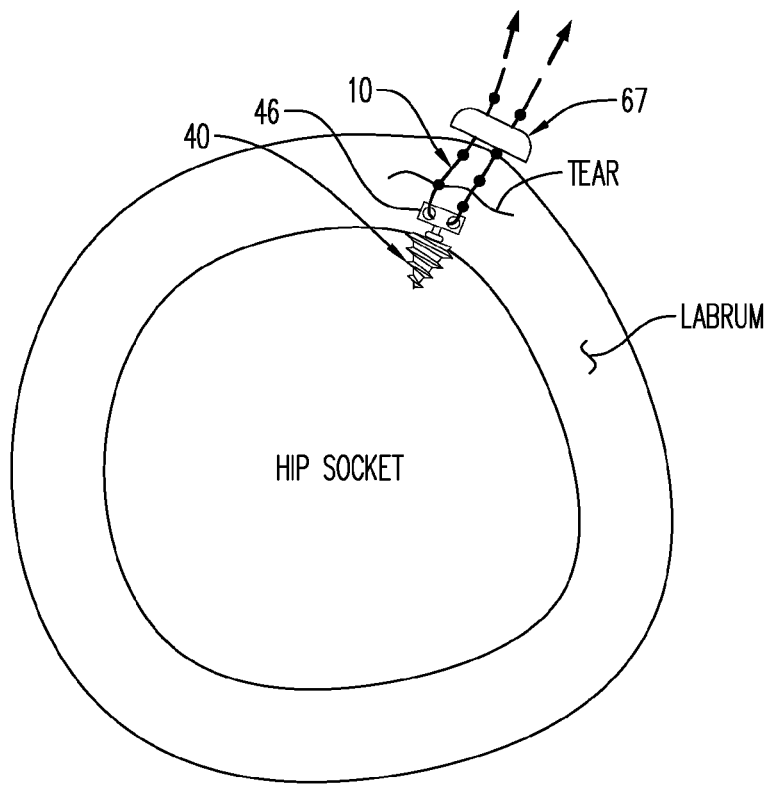

FIG. 15 is a simplified section view showing another aspect of the invention utilized to repair a tear in the hip labrum.

Figure 16:
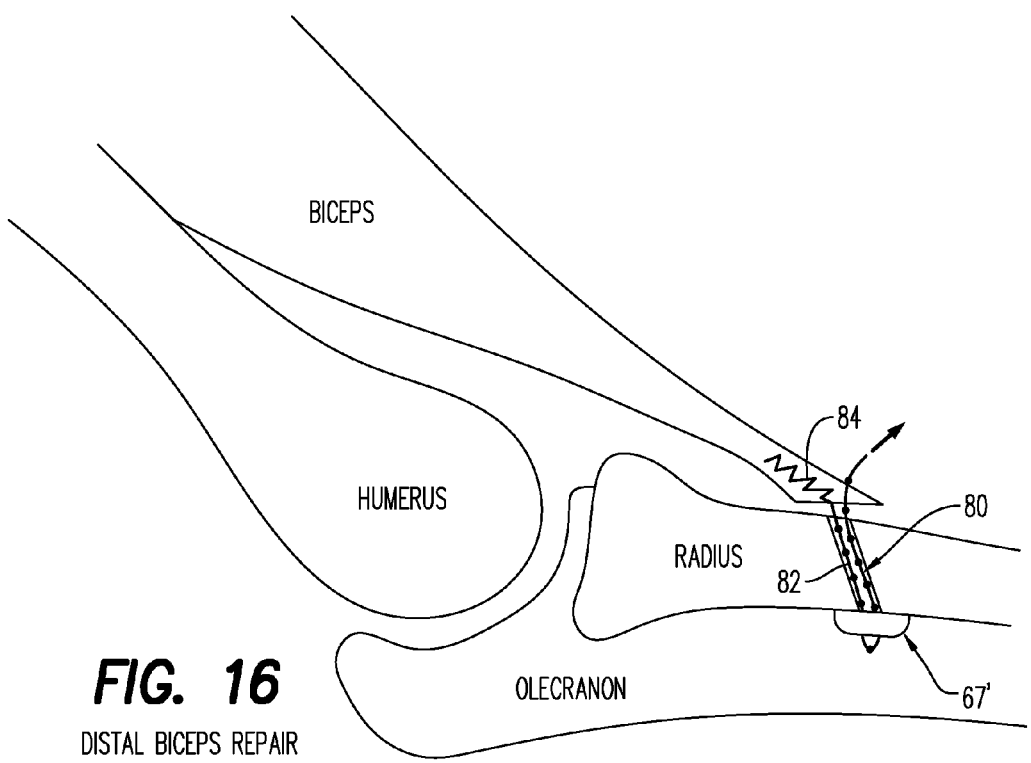

FIG. 16 depicts another aspect of the invention utilized to reattach the torn distal end of the biceps.

Figure 17:
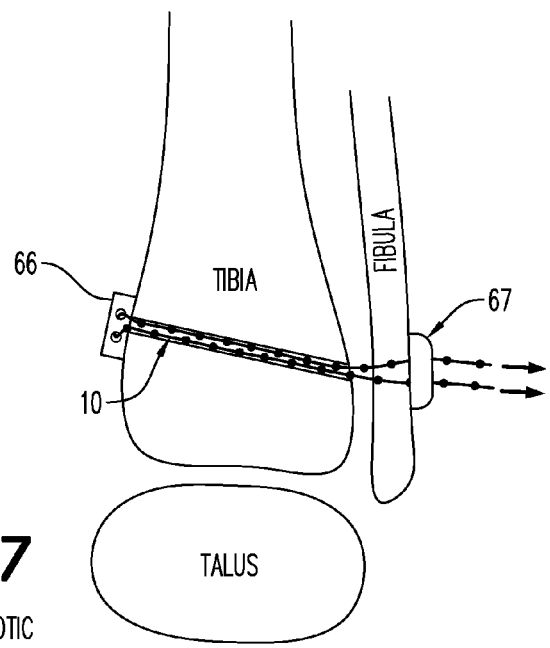

FIG. 17 shows a schematic view utilizing another aspect of the invention to reattach the fibula of an ankle syndesmotic disruption.

FIG. 18 is a side elevation view depicting another aspect of the invention for reattaching the proximal biceps tendon to the humeral head.

FIG. 19 is a simplified section view depicting another aspect of the invention for repairing a tear in the joint capsule which surrounds a shoulder socket.

FIG. 20 is an enlargement of area 20 in FIG. 19.

Figure 21:
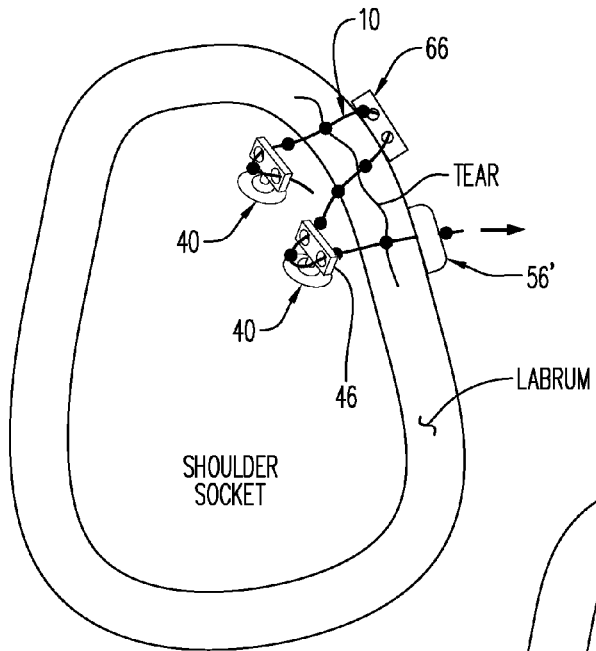
Figure 22:
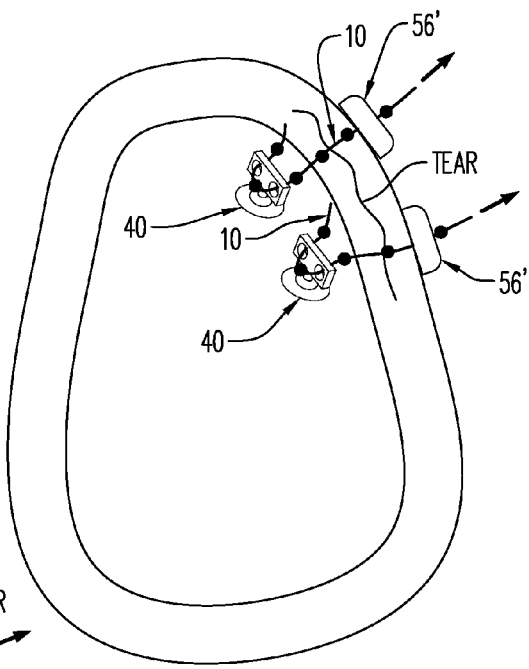
Figure 23:
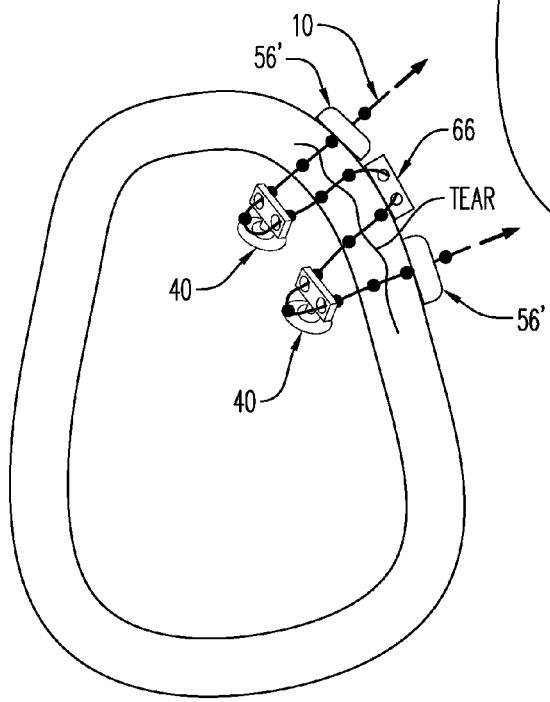

FIGS. 21 to 23 show other aspects of the invention utilized to repair a tear in the shoulder labrum surrounding a shoulder socket.

FIG. 24 is a simplified side elevation view showing another aspect of the invention utilized to effect a coracoclavicular ligament repair.

FIG. 25 is an elevation view utilizing another aspect of the invention to effect a subscapularis-to-humeral head repair.

FIG. 26 is a section view in the direction of arrows 26-26 in FIG. 25.

FIG. 27 is an elevation view showing another aspect of the invention utilized to reattach a rotator cuff tendon to the top of the humerus.

FIG. 28 and FIG. 29 depict alternate aspects of the invention utilized to effect the repair shown in FIG. 27.

Figure 30:
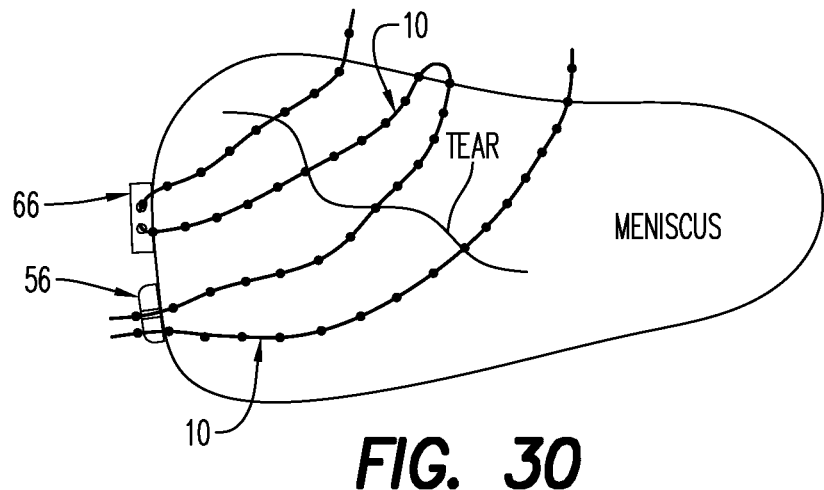
Figure 31:
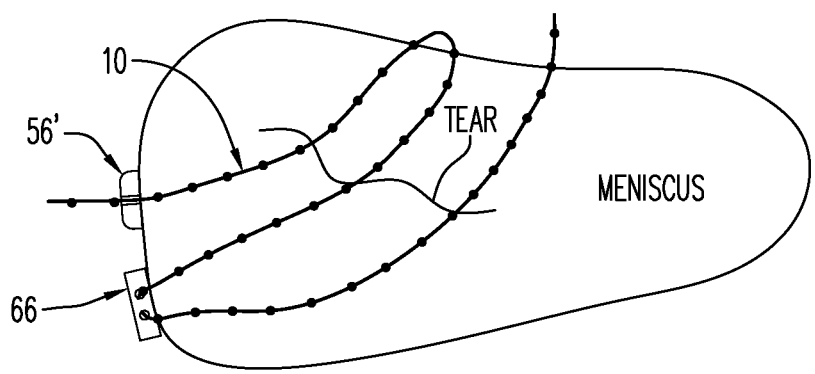

FIGS. 30 and 31 depict sagittal views depicting alternate aspects of the invention utilized to effect a meniscus tear repair.

Figure 32:
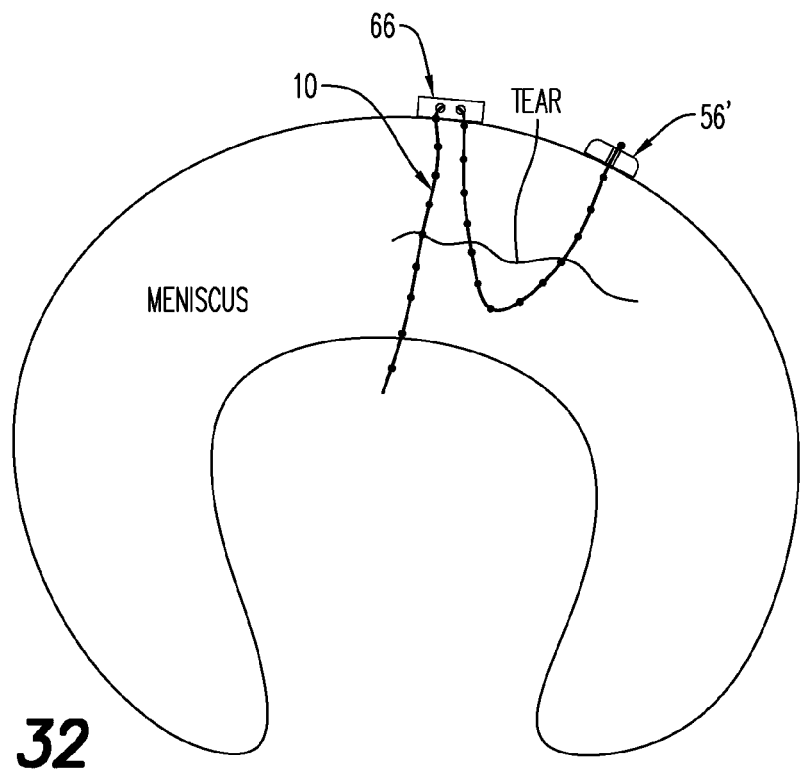
Figure 33:
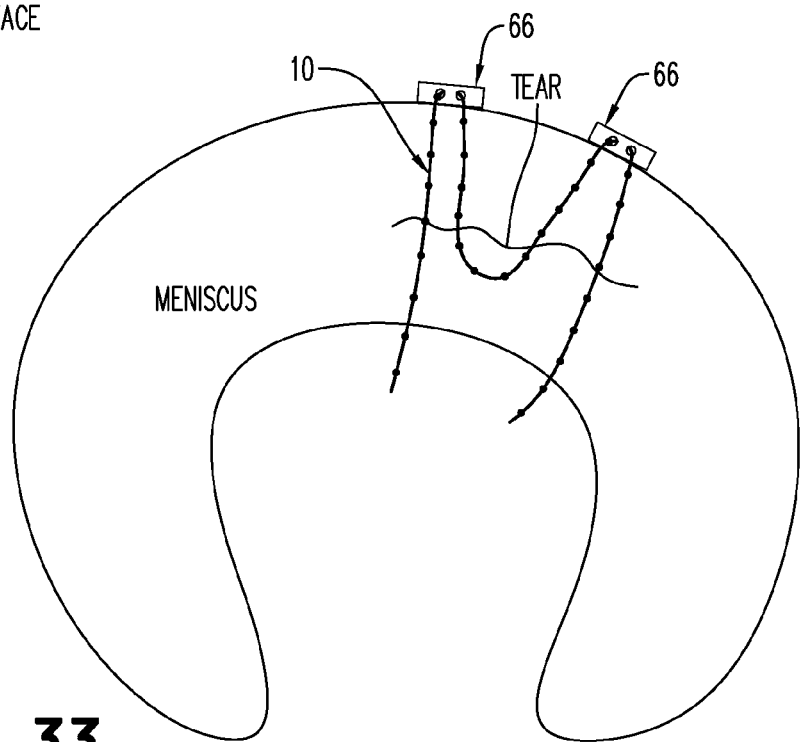

FIGS. 32 and 33 depict alternate aspects of the invention utilized to effect a torn meniscal repair.

Figure 34:
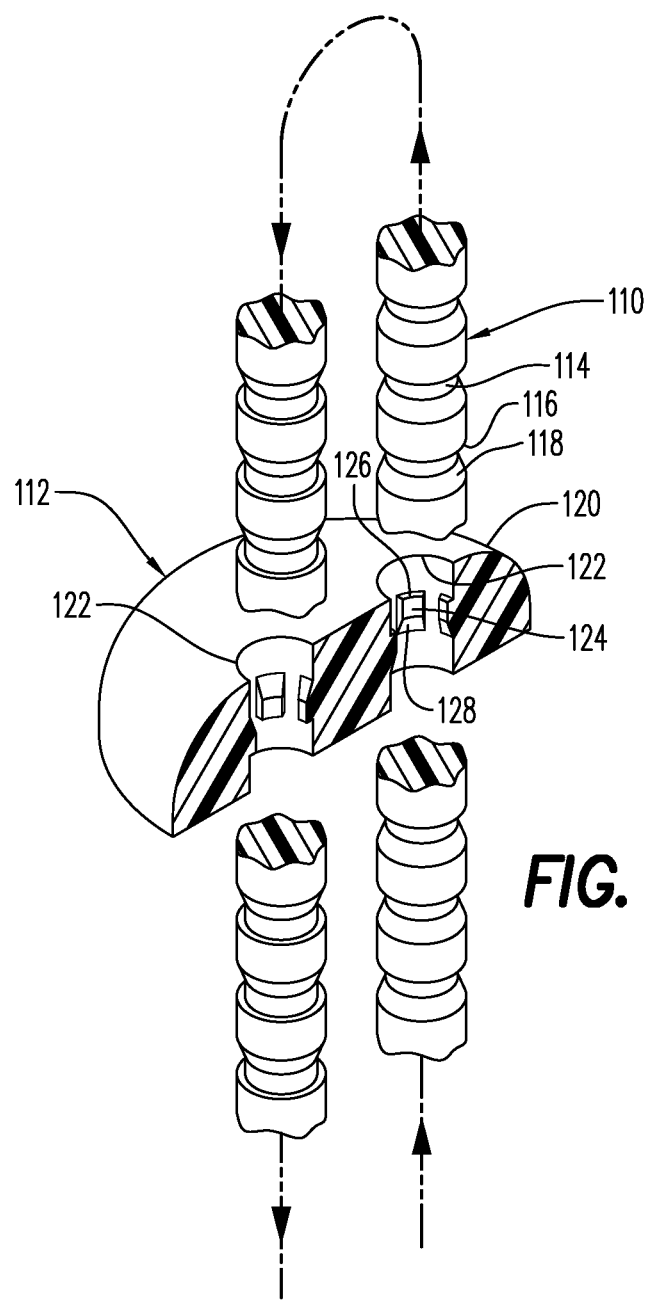

FIG. 34 is a broken perspective view of another embodiment of a suture operatively engaged with cooperatively structured suture tissue restraint.

FIGS. 35 to 38 are perspective views of other embodiments of a suture anchor.

FIG. 39 is an enlarged view of area 206 of FIG. 38.

FIG. 39A is an alternate embodiment of area 206 in FIG. 39.

FIG. 40 shows several alternate cross-sections in the direction of arrows 40-40 in FIG. 39.

FIGS. 41 to 47 are each side elevation views of other embodiments of suture anchors.

FIGS. 48 to 52 are perspective views of additional exemplary configurations of sutures.

FIG. 53 is a perspective view of another embodiment of a suture tissue restraint.

FIG. 53A is a view of FIG. 53 depicting alternate positions of suture 10 engaged therein.

FIG. 54 is a top plan view of FIG. 53.

Figure 55:
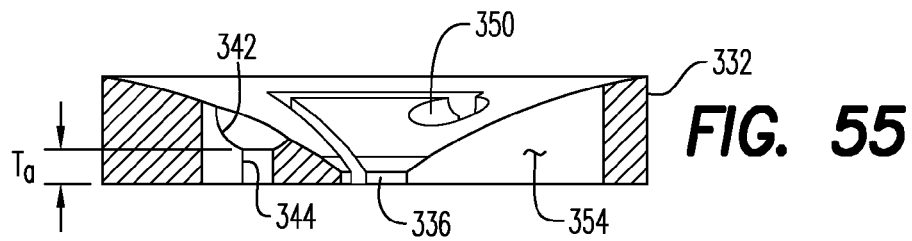

FIG. 55 is a section view in the direction of arrows 55-55 in FIG. 54.

Figure 56:
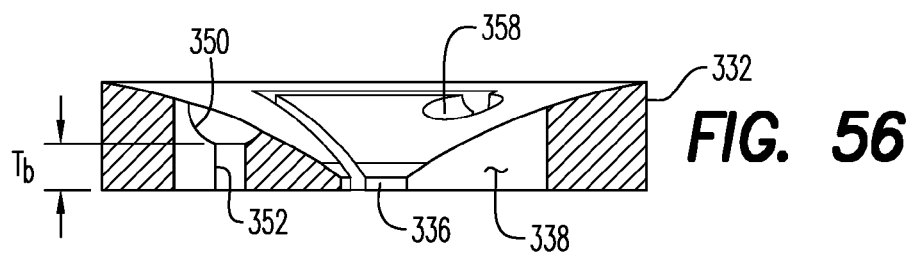

FIG. 56 is a section view in the direction of arrows 56-56 in FIG. 54.

Figure 57:
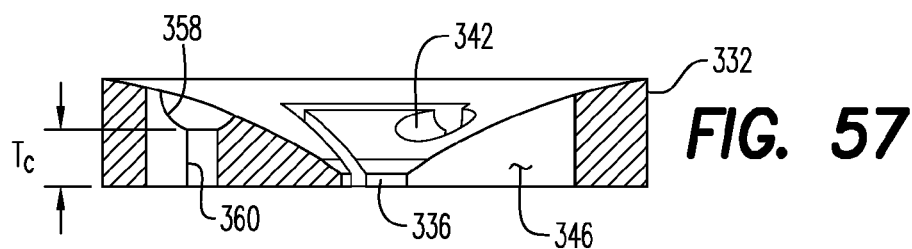

FIG. 57 is a section view in the direction of arrows 57-57 in FIG. 54.

Figure 58:
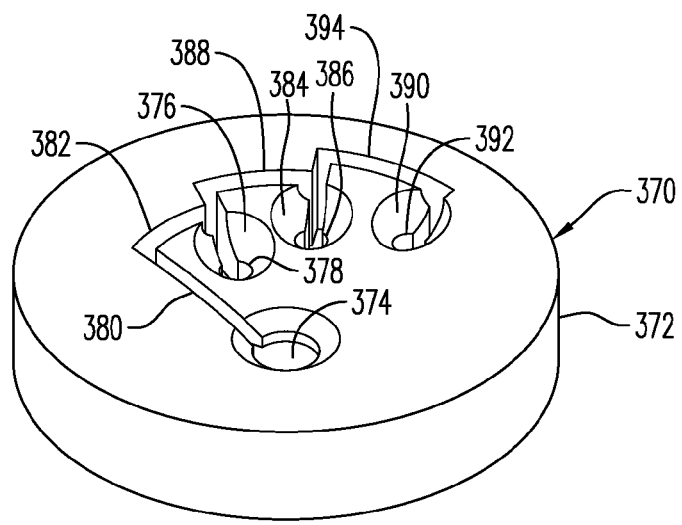

FIG. 58 is a perspective view showing an alternate embodiment of the suture tissue restraint shown in FIG. 53.

Figure 59:
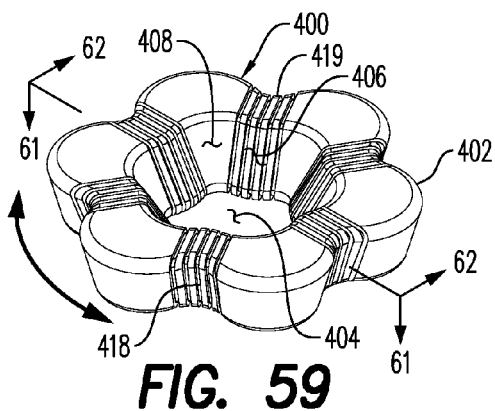

FIG. 59 is a perspective view of an expandable suture tissue restraint.

Figure 60:
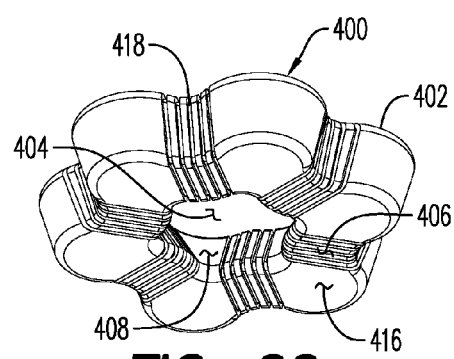

FIG. 60 is another perspective view of the suture tissue restraint shown in FIG. 59.

Figure 61:
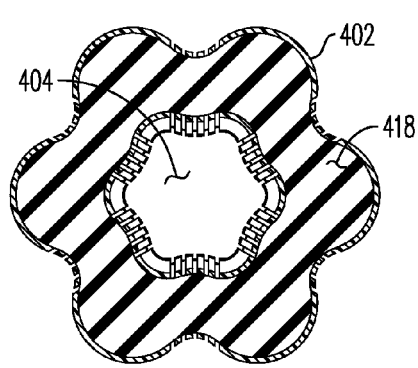

FIG. 61 is a section view in the direction of arrows 61-61 in FIG. 59.

Figure 62:
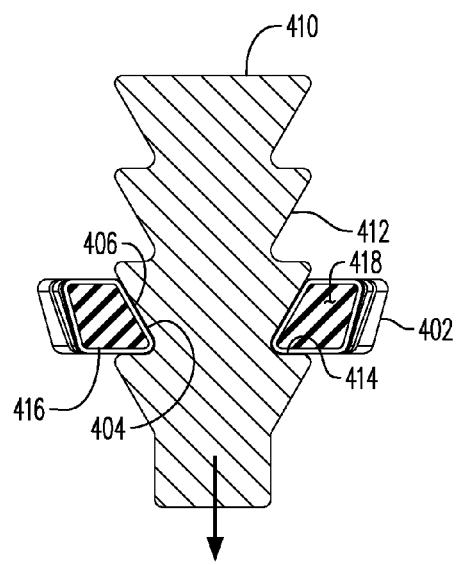

FIG. 62 is a section view in the direction of arrows 62-62 in FIG. 59 and including an interlock suture 410 therein.

Figure 63:
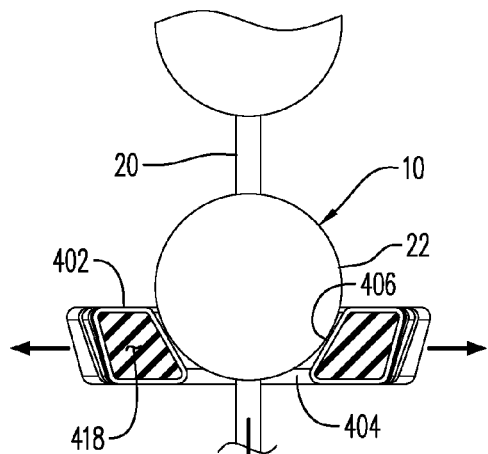

FIG. 63 is a view similar to FIG. 62 showing another suture 20 lockingly engaged therein.

Figure 64:
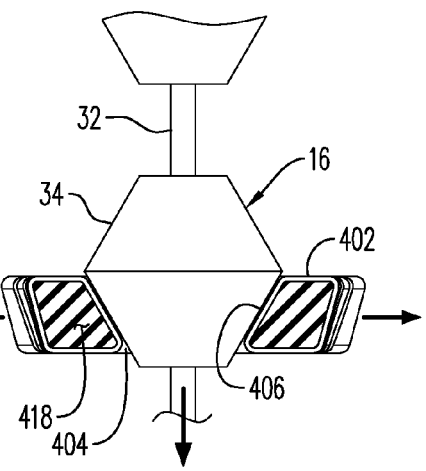

FIG. 64 is yet another view of FIG. 62 showing yet another suture 32 lockingly engaged therein.

Figure 65:
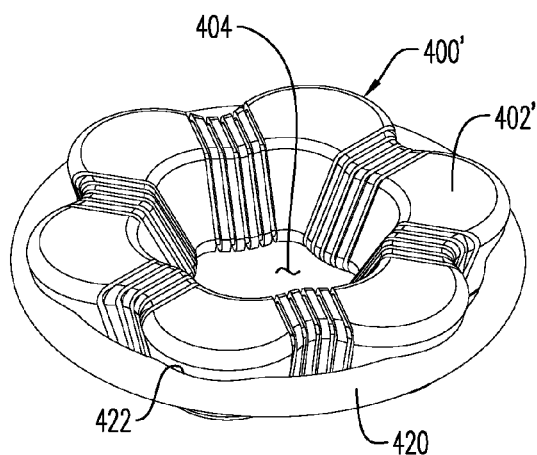
Figure 66:
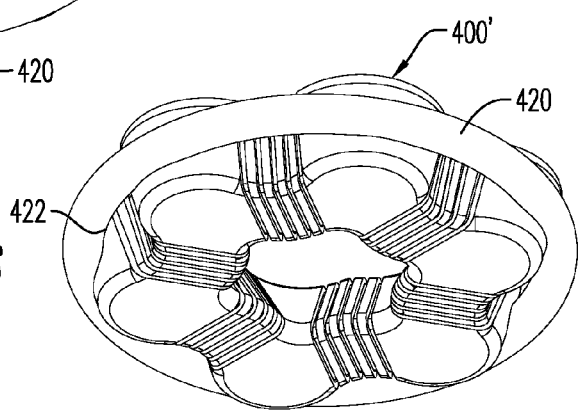

FIGS. 65 and 66 are perspective views of an alternate embodiment of the suture tissue restraint 400 shown in FIGS. 59 and 60, respectively.

Figure 67:
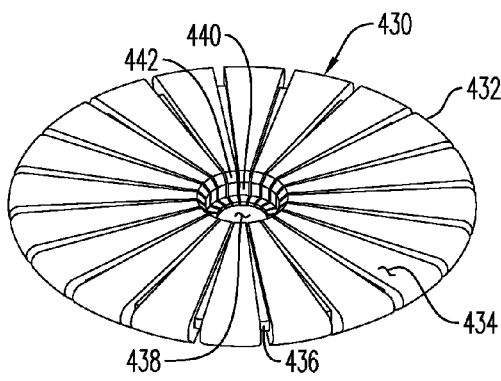
Figure 68:
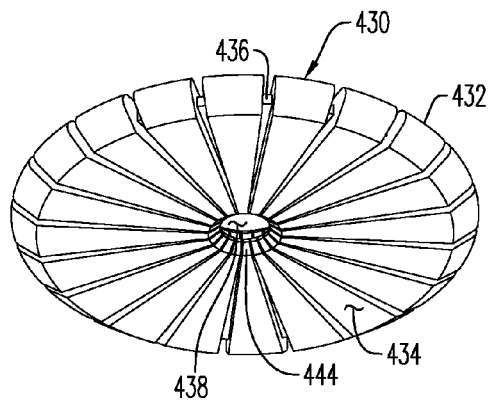

FIGS. 67 and 68 are perspective views of another embodiment of a suture tissue restraint.

Figure 69:
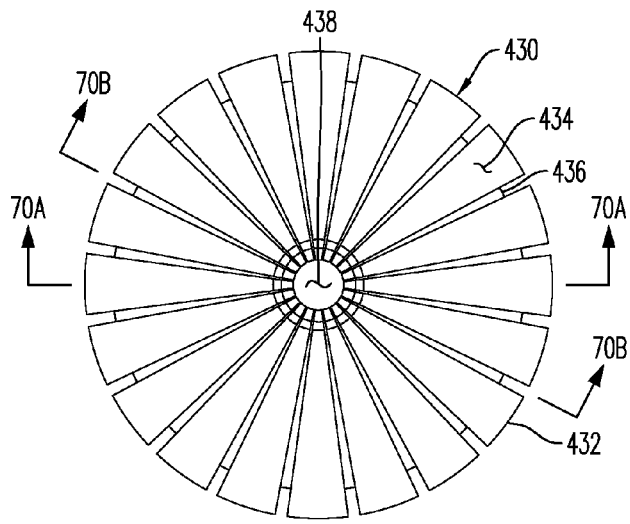

FIG. 69 is a top plan view of FIG. 67.

Figure 70A:
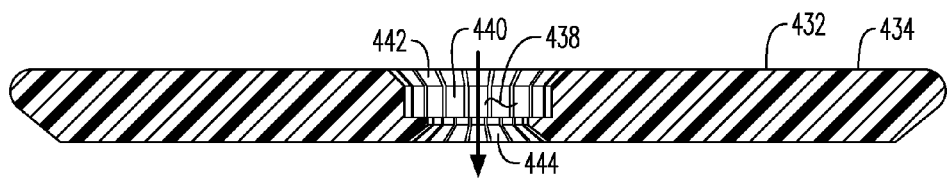
Figure 70B:
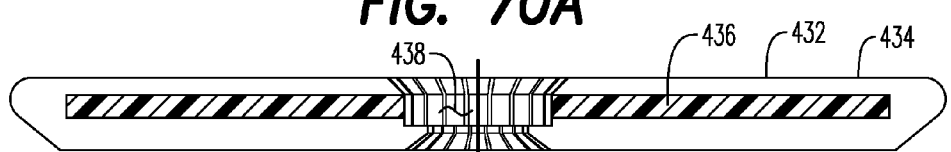

FIGS. 70A and B are section views in the direction of arrows 70A-70A and 70B-70B in FIG. 69.

Figure 71:
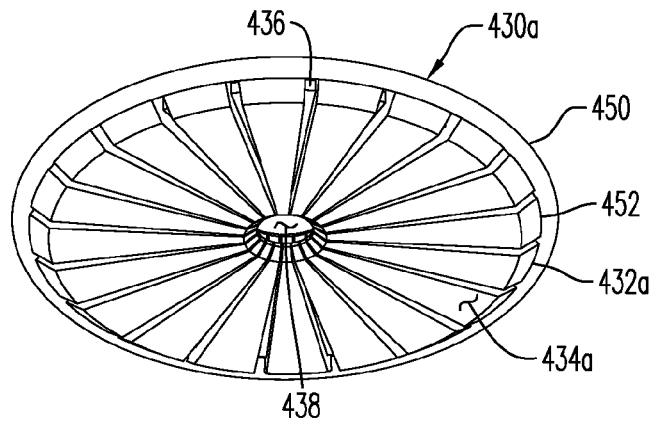

FIG. 71 is an alternate embodiment of the suture tissue restraint 430 shown in FIG. 67.

Figure 72:
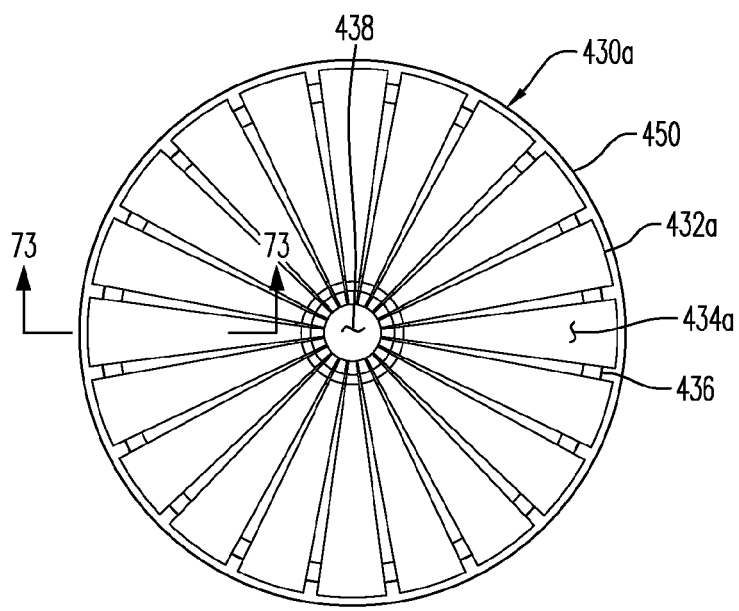

FIG. 72 is a top plan view of FIG. 71.

Figure 73:
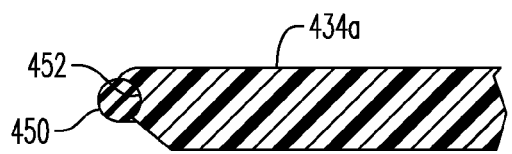

FIG. 73 is a section view in the direction of arrows 73-73 in FIG. 72.

Figure 74:
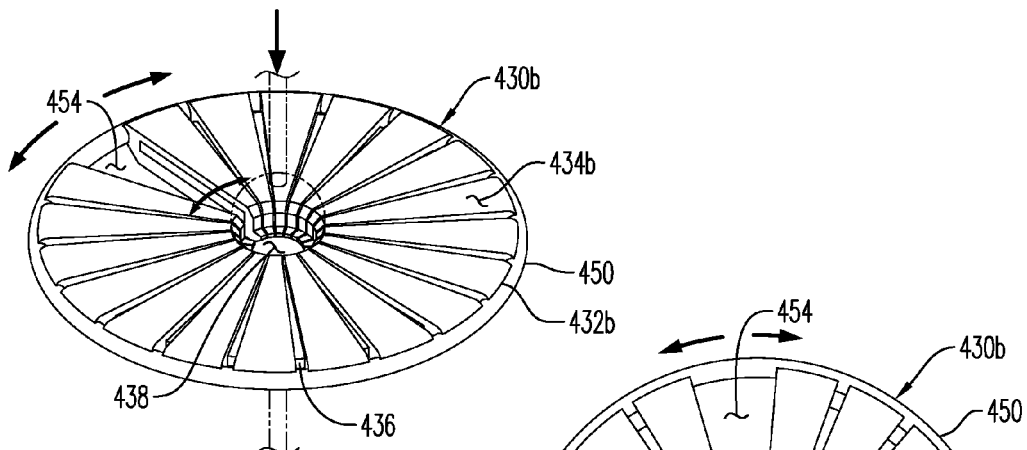

FIG. 74 is a perspective view of an alternate embodiment of FIG. 71.

Figure 75:
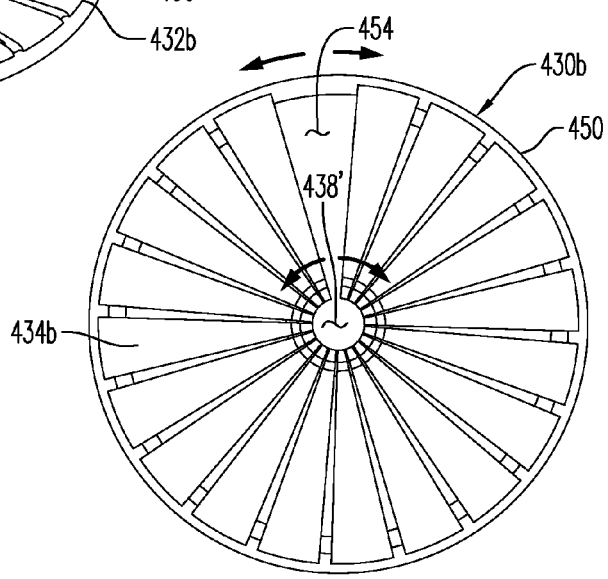

FIG. 75 is a top plan view of FIG. 74.

Figure 76:
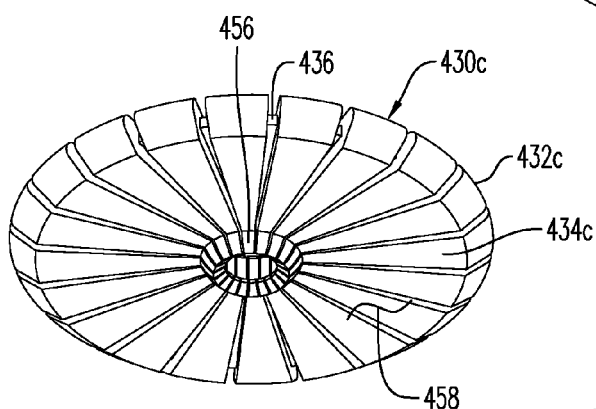
Figure 76A:
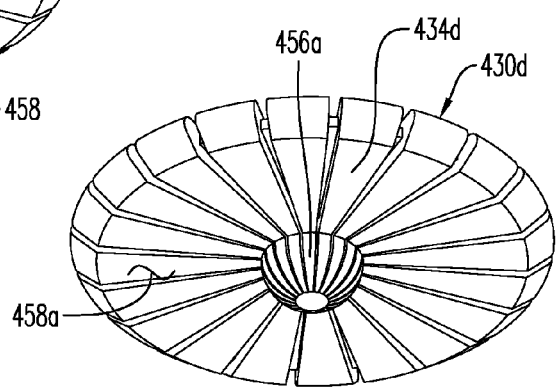

FIGS. 76 and 76A are perspective views of alternate embodiments of the suture tissue restraint shown in FIG. 68.

FIGS. 77 to 82 are side elevation views of alternate embodiments of additional sutures engaged within suture tissue restraints.

Figure 77:
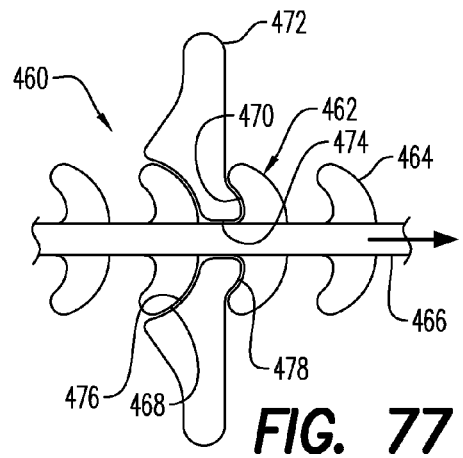
Figure 78:
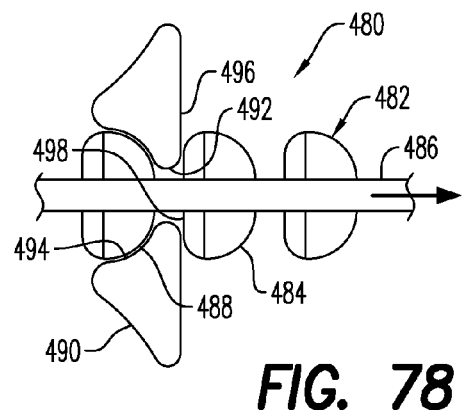
Figure 79:
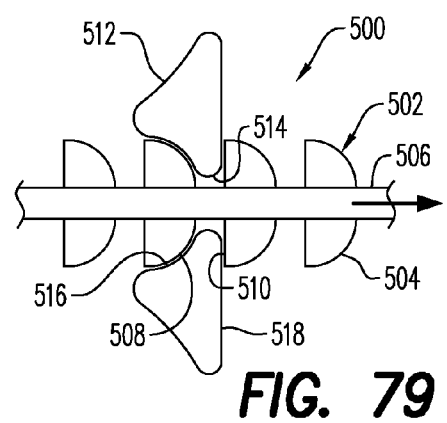
Figure 80:
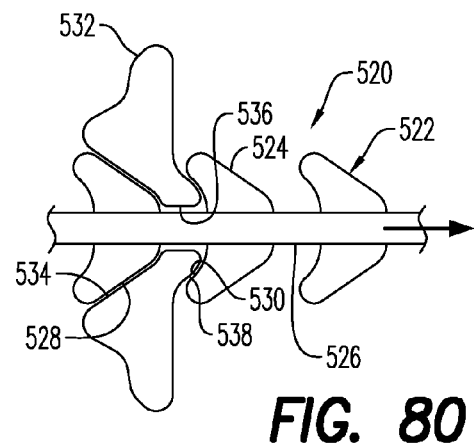
Figure 81:
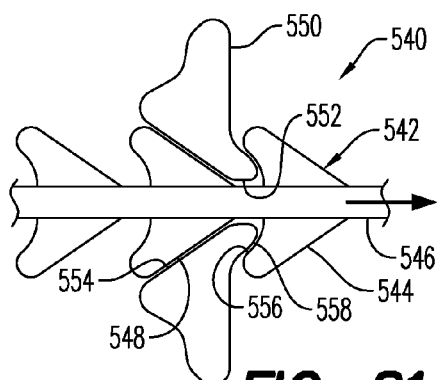
Figure 82:
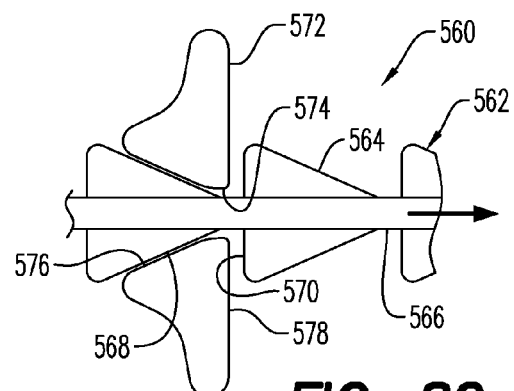
Figure 83:
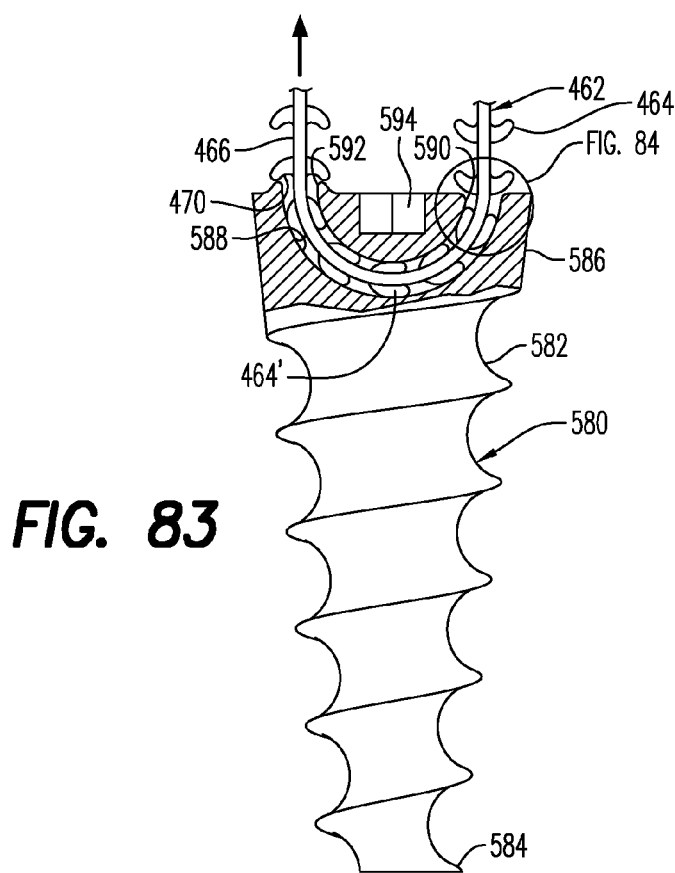

FIG. 83 is a side elevation broken view of another alternate embodiment of the tissue anchor and suture 462 of FIG. 77.

Figure 84:
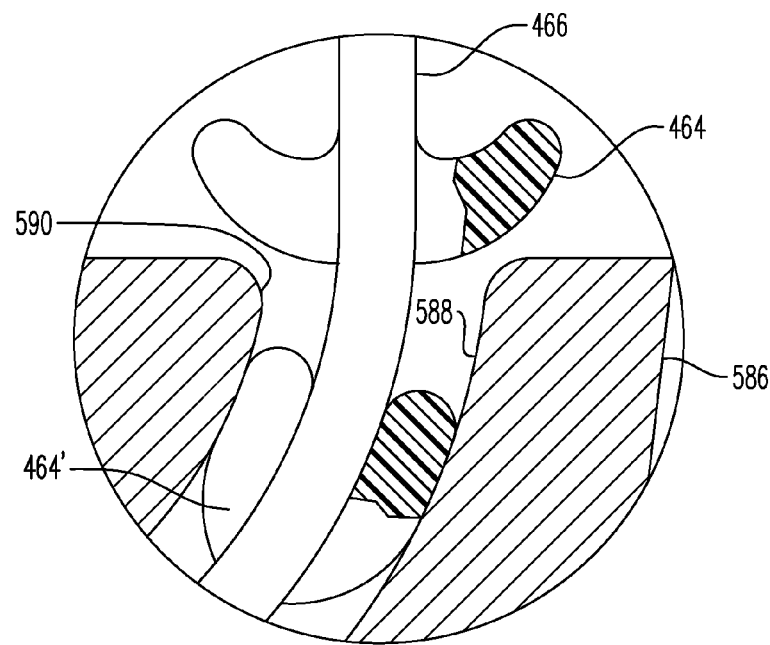

FIG. 84 is an enlargement of area FIG. 84 in FIG. 83.

Exemplary embodiments are illustrated in reference figures of the drawings. It is intended that the embodiments and figures disclosed herein are to be considered to be illustrative rather than limiting.

DETAILED DESCRIPTION OF THE INVENTION

Figure 1:
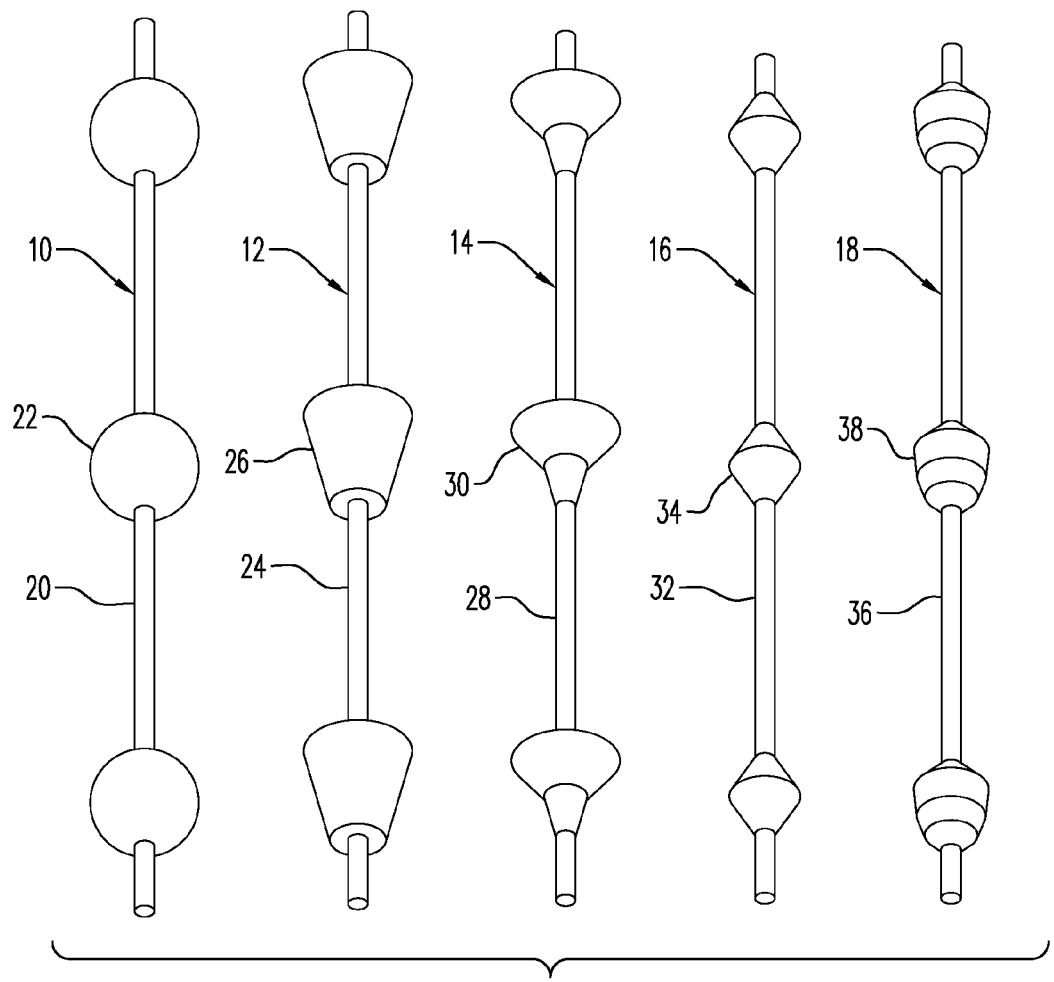
FIG. 1 is a perspective of a plurality of exemplary configurations of sutures each having spaced apart locking protuberances.

Nomenclature 10. suture
12. suture
14. suture
16. suture
18. suture
20. suture strand
22. bead-shaped protuberance
24. suture strand
26. truncated conical protuberance
28. suture strand
30. two-step conical protuberance 32. suture strand
34. symmetric conical protuberance
36. suture strand
38. segmented bullet-shaped protuberance
40. tissue anchor
41. tissue anchor
42. conical anchor body
43. tissue anchor
44. conical anchor body
45. suture entry cavity
46. suture engagement bar
47. suture exit cavity
48. suture locking aperture
49. suture one-way restriction
50. anchor post
51. suture anchor
52. anchor post cavity
53. suture entry aperture
54. tissue anchor top surface
55. suture exit aperture
56. suture tissue restraint
57. suture transverse passage
58. suture locking aperture
59. tissue gripping member
60. suture one-way lock
61. tissue anchor
62. tissue contact surface
63. tissue engaging member
64. suture severance point
65. suture locking aperture
66. suture tissue restraint
67. suture tissue restraint
68. suture locking aperture
69. aperture bevel
70. suture engagement bar
71. suture clearance aperture
72. tissue contact surface
74. open outer surface
76. tissue gripping member
78. suture clearance aperture
80. suture
82. suture strand
84. suture bare strand segment
86. hip prosthesis
88. suture locking aperture
96. orthopedic plate
98. anchor screw holes
100. suture locking aperture
102. tissue gripping member
104. suture clearance aperture
106. suture loop lock
108. suture locking aperture
110. grooved suture
112. suture tissue restraint
114. locking groove
116. groove locking edge
118. groove ramped edge
120. body
122. suture locking aperture
124. locking protuberance
126. locking edge
128. ramped edge
130. tissue anchor
132. tapered spiral thread
134. head
136. tissue penetrating tip
138. driving socket
140. suture one-way restriction
142. suture entry cavity
144. suture exit cavity
150. tissue anchor
152. tapered spiral coil
154. head
156. tissue penetrating tip
158. driving socket
160. suture one-way restriction
162. suture entry cavity
164. suture exit cavity
170. tissue anchor
172. spiral coil
174. head
176. tissue penetrating tip
178. driving socket
180. suture one-way restriction
182. suture entry cavity
184. suture exit cavity
190. tissue anchor
192. tapered spiral coil
192a-h. alternate tapered spiral coils
194. head
196. tissue penetrating tip
198. driving socket
200. suture one-way restriction
202. suture entry cavity
204. suture exit cavity
206. spiral coil segment
206a. spiral coil segment
208. tissue cutting edge
208a-g. tissue cutting edge
210. tissue anchor
212. tapered spiral coil
214. head
216. tissue penetrating tip
218. driving socket
220. suture one-way restriction
222. suture entry cavity
224. suture exit cavity
226. centering shaft
228. tip
230. tissue anchor
230'. tissue anchor
232. tapering spiral coil
234. solid tapered screw
236. head
238. tissue penetrating tip
240. driving socket
242. suture one-way restriction
244. suture entry cavity
246. suture exit cavity
248. centering shaft
249. tip
250. tissue anchor
250'. tissue anchor
252. tapered spiral coil
254. solid tapered screw
256. head
258. tissue penetrating tip
260. driving socket
262. suture one-way restriction
264. suture entry cavity
266. suture exit cavity
268. centering shaft
270. tissue anchor
270'. tissue anchor 272. solid tapered screw
274. tapered spiral coil
276. solid tapered screw
278. head
280. tissue penetrating tip
282. driving socket
284. suture one-way restriction
286. suture entry cavity
288. suture exit cavity
289. centering shaft
290. suture
292. suture strand
294. dome-shaped protuberance
296. suture
298. suture strand
300. mushroom-shaped protuberance
302. cavity
304. suture
306. suture strand
308. cup-shaped protuberance
310. cavity
312. suture
314. suture strand
316. quarter protuberance
320. suture
322. arrow protuberance
324. arrow protuberance
326. tip
330. suture tissue restraint
332. disc-shaped body
336. flexible suture passage aperture
338. radial slot
340. concentric slot
342. suture socket
344. suture strand aperture
346. radial slot
348. concentric slot
350. suture socket
352. suture strand aperture
354. radial slot
356. concentric slot
358. suture socket
360. suture strand aperture
370. suture tissue restraint
372. disc-shaped body
374. suture passage aperture
376. suture socket
378. suture strand aperture
380. radial slot
382. concentric slot
384. suture socket
386. suture strand aperture
388. concentric slot
390. suture socket
392. suture strand aperture
394. concentric slot
400. expandable suture tissue restraint
400'. expandable suture tissue restraint
402. solid segment
404. expandable suture locking aperture
406. expandable aperture segment
408. rigid aperture segment
410. suture
412. conical protuberance
414. locking surface
416. suture bearing surface
418. resilient layer
419. rigid layer
420. resilient O-ring
422. annular groove
430. expandable suture tissue restraint
430a-c. expandable suture tissue restraints
432. disc-shaped body
432'. disc-shaped body
434. rigid sector
436. resilient sector
438. expandable suture locking aperture
440. cylindrical aperture segment
442. aperture inlet segment
444. aperture outlet segment
450. resilient O-ring
452. annular groove
452'. annular groove
454. empty sector
456. tapered segment
456a. semi-spherical segment
458. tissue contact surface
460. suture/tissue restraint
462. suture
464. resilient mushroom protuberance
466. suture strand
468. suture deforming surface
470. suture locking surface
472. suture tissue restraint
474. suture aperture
476. restraint deforming surface
478. restraint locking surface
480. suture and tissue restraint
482. suture
484. resilient suture protuberance
486. suture strand
488. suture deforming surface
490. suture tissue restraint
492. suture strand aperture
494. restraint deforming surface
496. restraint locking surface
498. suture locking surface
500. suture and tissue restraint
502. suture
504. resilient suture protuberance
506. suture strand
508. suture deforming surface
510. suture locking surface
512. suture tissue restraint
514. suture aperture
516. restraint deforming surface
518. restraint locking surface
520. suture and tissue restraint
522. suture
524. resilient cone-shaped protuberance
526. suture strands
528. suture deforming surface
530. suture locking surface
532. suture tissue restraint
534. restraint deforming surface
536. suture aperture
538. restraint locking surface
540. suture and tissue restraint
542. suture
544. arrow-shaped protuberance
546. suture strand
548. suture deforming surface
550. suture tissue restraint
552. suture aperture 554. restraint deforming surface
556. suture locking surface
558. restraint locking surface
560. suture and tissue restraint
562. suture
564. arrow-shaped protuberance
566. suture strand
568. suture deforming surface
570. suture locking surface
572. suture tissue restraint
574. suture aperture
576. restraint deforming surface
578. restraint locking surface
580. tissue anchor
582. tapered spiral thread
584. tissue penetrating tip
586. head
588. suture passage
590. head deforming inlet surface
592. head locking surface
594. driving socket Referring now to the drawings, and firstly to FIG. 1, a number of exemplary elongated flexible sutures shown generally at numerals 10, 12, 14, 16 and 18. These sutures are preferably formed of flexible or semi-flexible medically implantable material. Each of these sutures include longitudinally spaced, enlarged-in-diameter segments or protuberances 22, 26, 30, 34 and 38 formed along the length of the corresponding slender suture strand 20, 24, 26, 38 and 36.

Suture 10 is formed having protrusions 22 which are substantially spherical or bead-shaped. Suture 12 includes the protuberances 26 which are in the form of a truncated cone, while suture 14 includes protuberances having a two-step truncated conical structure. Suture 16 includes protuberances 34 having opposing truncated conical portions forming each of the protuberances, while suture 18 has a gradual three step enlargement to each of the protuberances, ending in a sharply truncated conical end or tail portion thereof to interact with suture locking apertures described below.

Referring now to FIGS. 2 to 4, one embodiment of a tissue anchor within the scope of this invention is there shown generally at numeral 40 and is formed of a medically implantable material. This tissue anchor 40 includes a conical anchor body 42 having outwardly extending spiral threads which tightly lockingly engage into a tissue substrate such as bone or cartilage. As with all of the tissue anchors and suture tissue restraints disclosed within the scope of this invention, this tissue anchor 40 includes a suture engagement bar 46 having a pair of closely spaced apart suture locking apertures 48 which are sized in diameter and having one end thereof beveled so that, as will be described in detail herebelow, restrict an appropriately configured suture as described in FIG. 1 hereinabove to pass snugly through each of the suture locking apertures 48 in only direction. That is to say that the suture may be drawn into each of the suture locking apertures 48 and pulled therethrough in one direction, but reversal of movement of the suture within these suture locking apertures 48 is prohibited or substantially inhibited so as to effect a locking position in one-way movement fashion of the suture therethrough.

The suture engagement bar 46 includes an anchor post 50 which snappingly and lockingly engages into a mating anchor post cavity 52 formed into the enlarged head proximal end of the anchor body 42 so that the suture engagement bar 46 may be rotated about the longitudinal axis of the anchor body 42 relatively freely so as to quickly and easily rotationally orient the suture engagement bar 46 to a neutral tension force applied by the suture when tightened.

Referring now to FIG. 4A, an alternate embodiment of the tissue anchor 40 is there shown at numeral 40' wherein the entire suture engagement bar 46 is recessed flush with the upper enlarged top surface 54 of the anchor body 42'. Thus, once the suture has been passed through the suture locking apertures 48 after the suture engagement bar has been snappingly engaged into anchor post cavity 52' and the anchor post 50 has been thusly secured therewithin, the top or outer edge of the suture engagement bar 46 is substantially even with the enlarged top surface 54 of the tissue anchor 40'.

Referring now to FIGS. 5 and 5A, yet another embodiment of the tissue anchor is there shown generally at numeral 43. This tissue anchor 43 includes a conical anchor body 44 having outwardly extending spiral threads and a fixed transverse suture engagement bar 46' which is secured within a circular cavity formed into the head of the anchor body 44. Again, the suture engagement bar 46' includes two spaced suture locking apertures 48' each having cooperatively oriented bevels so that a selected suture will pass in only direction through the pair of suture locking apertures 48'. This embodiment 43 affords a one-piece structure with the suture engagement bar 46' secured in place and in flush alignment with the head of the anchor body 44 which is the preferred configuration of a tissue anchor of this type.

Although not shown in FIGS. 2 to 5, the head of each of the tissue anchors will be provided with tightening cavities formed into the enlarged end of the anchor body so that a separate tool may be used to drivingly engage the spiral threads into the appropriate bone or cartilage substrate. The tissue anchor 43 in FIGS. 5 and 5A may be rotationally drivingly engaged into the tissue substrate by engagement of an appropriately configured tool onto the suture engagement bar 46' which is rigidly secured in the position shown.

Figure 5B:
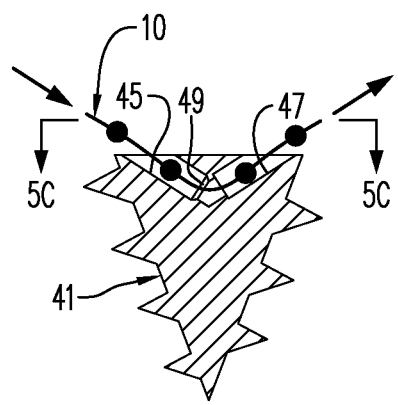
FIG. 5B is a section view of another alternate embodiment of the suture anchor of FIG. 2.
Figure 5C:
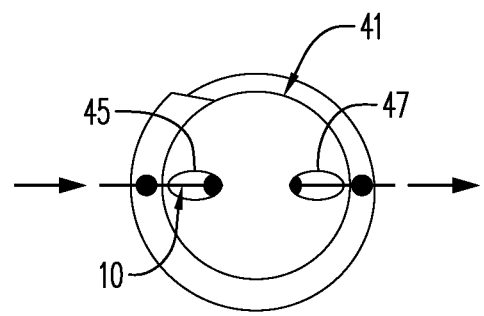
FIG. 5C is a top plan view in the direction of arrows 5C-5C in FIG. 5B.

In FIGS. 5B and C, another configuration of a tissue anchor 41 is there shown configured similarly to the tissue anchors 40, 40' and 43 previously described. However, this tissue anchor 41 includes diagonally oriented intersecting apertures 45 and 47 which converge centrally of the anchor body adjacent to the enlarged head thereof and are sized to receive and permit only one-way movement of the suture 10 in the direction of the arrows. A one-way restriction 49 is provided so as to insure that, once tightened by pulling in the direction of the arrows, the suture 10 may not be moved in the opposite direction.

Figure 5D:
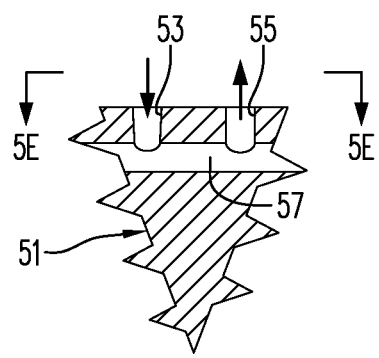
FIG. 5D is yet another alternate embodiment of the suture anchor of FIG. 2.
Figure 5E:
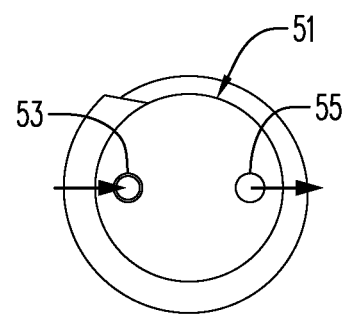
FIG. 5E is top plan view in the direction of arrows 5E-5E in FIG. 5D.

In FIGS. 5D and E, yet another tissue anchor is there shown generally at numeral 51 which also includes a pair of spaced parallel suture entry and exit apertures 53 and 55 which are interconnected by a transverse passage 57. The suture entry aperture 53 is beveled and tapered so as to facilitate only one-way movement of the suture therethrough and exiting from the suture exit aperture 55 only in the direction of the arrows shown.

Figure 6:
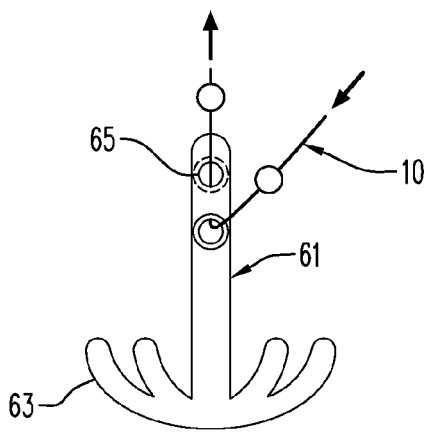
FIG. 6 is a side elevation view of another embodiment of a suture anchor of this disclosure.

Referring now to FIG. 6, another tissue anchor is there shown generally at numeral 61 formed of a medically suitable material having an elongated shank having two closely spaced apart suture locking apertures 65 and 67 formed therethrough and a plurality of circumferentially spaced radially extending tissue engaging members 63. The locking apertures 65 include oppositely oriented bevels so that the suture may be drawn through the pair of locking apertures 65 in only the direction of the arrows.

Figure 7:
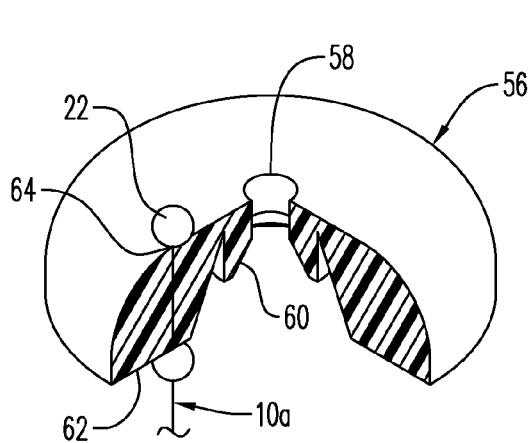
FIG. 7 is a broken perspective view of one embodiment of a suture tissue restraint.

Referring now to FIG. 7, one embodiment of a suture tissue restraint is there shown generally at numeral 56. This tissue restraint 56 may be formed of medically acceptable material. The body is domed-shaped having a flat tissue contact surface 62 and a central suture locking aperture 58 having a one-way suture lock 60 formed around the suture locking aperture 58 which prevents the suture from being drawn downwardly once a suture has been appropriately tensioned upwardly through the locking aperture 58. A second suture 10a is permanently connected through the body of the suture tissue restraint 56 extending downwardly from the flat tissue contact surface 62. However, the suture 10a may be cut at 64 and removed where a repair of tissue procedure only requires a single suture to be lockingly engaged within the suture locking aperture 58.

Figure 7A:
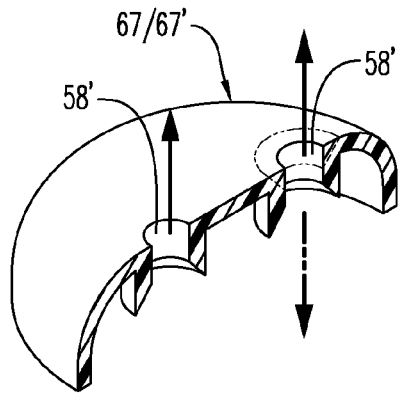
FIG. 7A is a broken perspective view of another embodiment of a suture tissue restraint.

In FIG. 7A, another suture tissue restraint is there shown generally at numeral 67 or 67' and formed having a domed-shaped body similar to that shown in FIG. 7. However, in this embodiment 67/67', two spaced apart suture locking apertures 58' are formed through the dome portion of the tissue restraint 67/67' in closely spaced relationship facing the tissue engaging side of this tissue restraint 67 so that a suture may be tensioned upwardly or away from the tissue contact surface. However, the bevels of the suture locking apertures 58' may be oriented oppositely one another to form suture tissue restraint 67' to lockingly engage a single suture for one directional movement only. Note that, if formed as shown without the missing portions, these suture tissue restraints may be snappingly engaged over a suture and they continue to function as above described.

Note that hereinbelow, tissue anchors and suture tissue restraints are sometimes collectively referred to as "tissue engaging members".

Figure 8:
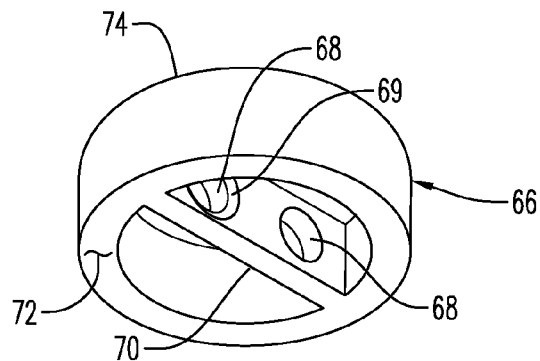
FIG. 8 is a broken perspective view of yet another embodiment of a tissue suture restraint.

Referring now to FIG. 8, another suture tissue restraint is there shown generally at numeral 66 having a ring-shaped body with a flat tissue contact surface 72 and an open outer surface 74. A transversely oriented suture engagement bar 70 formed as a unit with the ring-shaped body is also provided. Two spaced apart suture locking apertures 68 are oppositely beveled at 69 so as to provide the one-way locking engagement of a suture passing therethrough as previously described.

Figure 9:
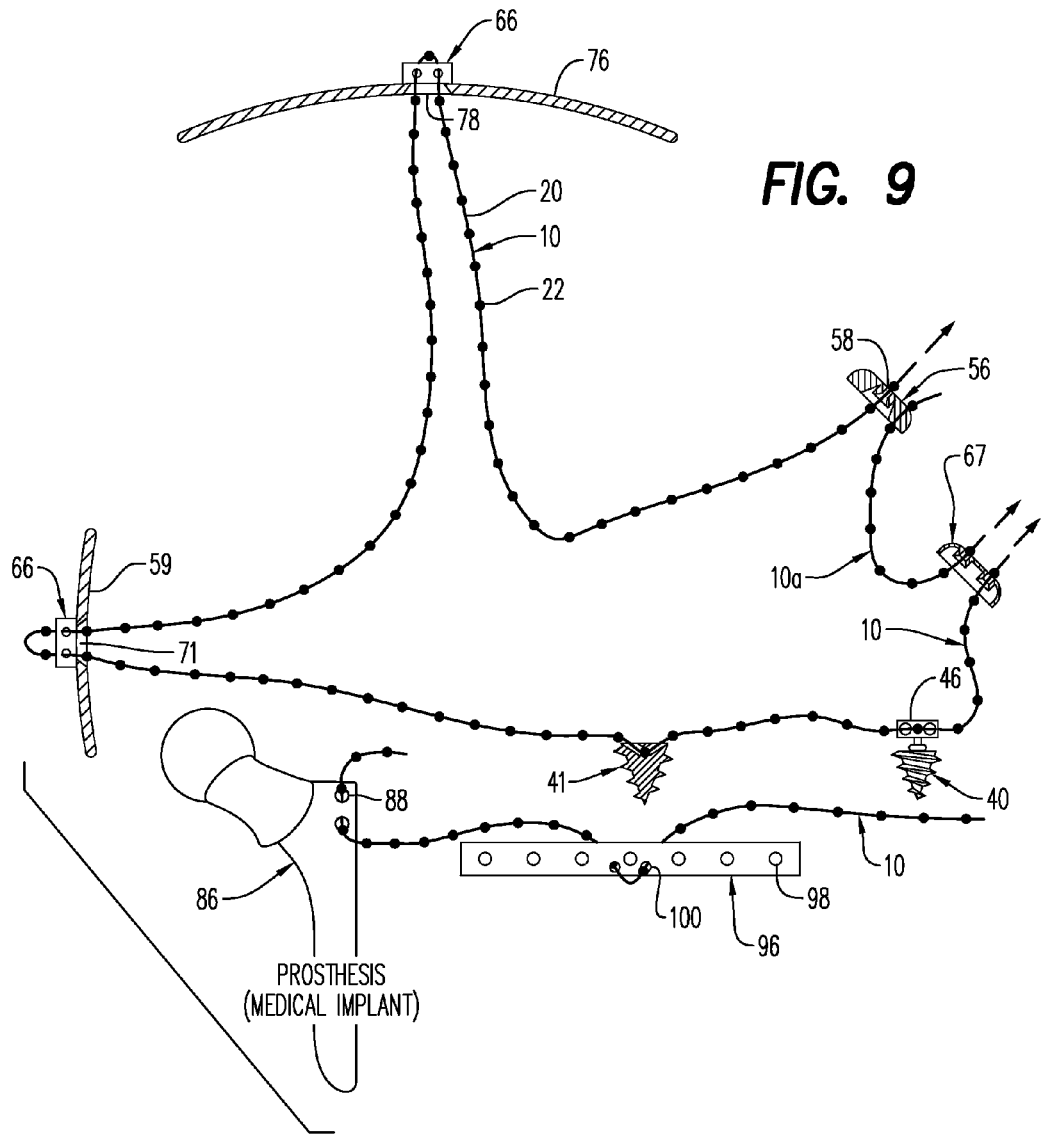
FIG. 9 is a pictorial view showing a variety of suture anchors and suture tissue restraints (absent tissue or tissue substrate for clarity) in locking engagement with one embodiment of the suture member 10 shown in FIG. 1.

Referring now to FIG. 9, a pictorial view showing a variety of tissue engaging members in relation to sutures 10 and 10a are there shown. The suture 10 is lockably engaged through the two spaced locking apertures of the suture tissue restraint 66 when positioned against a flexible tissue gripping member 59 which provides a larger tissue contact surface which will biasingly flex against the tissue or tissue substrate to maintain tension produced by the suture when suitably positioned through a suture clearance aperture 71 formed centrally through the tissue gripping member 59. Suture 10 is also shown passing through another suture clearance aperture 78 formed centrally through an enlarged tissue gripping member 76 and in one-way locking engagement with another suture tissue restraint 66.

The suture 10 also extends through the suture locking aperture of the suture tissue restraint 56 for tensioning of the suture in the direction of the arrow. The suture 10a which is permanently engaged at one end thereof into the body of the suture tissue restraint 56 as previously described then extends to one of the locking apertures of suture tissue restraint 67 while another portion suture 10 extends from the other locking aperture of the suture tissue restraint 67 for engagement through the dual locking apertures of the suture engagement bar 46 of the tissue anchor 40. This portion of suture 10 is then shown continuing on for locking engagement through suture entry and exit cavities 45 and 47 of tissue anchor 41 and then returning to the suture tissue restraint 66 through suture clearance aperture 71.

Still referring to FIG. 9, another suture 10 may also be lockingly passed through spaced locking apertures 100 formed through an elongated orthopedic plate 96 which is also provided with spaced anchor screw holes 98. Again, the spaced locking apertures 100 are cooperatively arranged and configured to allow for movement of the suture 10 in only direction therethrough. This suture 10 is shown continuing on to be lockingly engaged for one directional movement only through suture locking apertures 88 formed through a suitable portion of a typical hip prosthesis 86 or other medical implant, knee prosthesis, breast implant, cardiac pacemakers as examples but not to represent an all inclusive list, to which the suture 10 may be suitably anchored and tensioned as previously described.

Referring now to FIG. 10, another exemplary installation arrangement utilizing the elongated suture 10 is there shown. In this embodiment, the suture 10 is passed at each end thereof through the spaced locking apertures 68 of the suture tissue restraint 66 which is positioned against a flat enlarged tissue gripping member 102 formed of thin surgical steel or other suitable material and having a suture clearance aperture 104 formed therethrough positionable in alignment with the locking apertures 68 of the suture tissue restraint 66. A mid portion of the suture 10 is lockingly engaged for one directional movement only through the suture engagement bar 46 of the tissue anchor 40 as previously described.

In FIG. 11, a pictorial view of another aspect of the invention utilized to repair and restrain a broken distal phalanx of a finger metacarpal is there depicted. The suture 10 is lockingly passed through passageways drilled or formed through the broken bone ends, a mid portion of the suture 10 passing lockingly through the spaced locking apertures of the suture tissue restraint 66, each end of the suture 10 then lockingly passed through the suture tissue restraint 67 and tensioned in the direction of the arrows to secure the fracture for healing.

In FIG. 12, repair of a torn ACL tissue of a knee joint is there depicted. The suture 10 is passed through passageways formed in the femur and the tibia in aligned opposing fashion, a mid portion of the suture passing through the spaced locking apertures of the suture tissue restraint 66 and the free ends of the suture 10 lockingly engaged through the locking apertures formed through the suture tissue restraint 67.

In FIG. 13, a torn MCL of a knee joint is shown being repaired wherein a modified suture 80 having no protuberances along one end 84 thereof is shown surgically attached to the torn end of the MCL, the suture 80 then passing through spaced locking apertures of the suture engagement bar 46 of the tissue anchor 40 which has been previously secured into the lower end of the femur.

In FIG. 14, the repair of a torn medial patella-femoral ligament is there shown wherein one end 84 of a the suture 80 not having protuberances is surgically attached to the torn distal end of the ligament, the suture 80 then extending to the pair of locking apertures formed through the suture engagement bar 46 of tissue anchor 40 as previously described. The suture 80 then extends to the distal tip of the torn ligament passing therethrough and being secured in position by a suture tissue restraint 56', for added reattaching strength. The suture tissue restraint 56' is as previously described in FIG. 7 wherein the proximal protuberance 22 of suture 10a has been cleavered or cut at 64 and removed as being unnecessary.

The repair of a tear in a labrum surrounding a hip socket is shown in FIG. 15. The suture 10 is passed through the locking apertures of the suture engagement bar 46 of tissue anchor 40 which has previously been secured into the hip socket. The suture 10 is then passed through the tear and through the locking apertures of the surgical tissue restraint 67 and tensioned in the direction of the arrows to tighten and repair the tear.

In FIG. 16, the repair of a distal biceps which has become detached is there shown. A modified suture 80 which is absent protuberances at one end thereof at 84 is surgically attached to the distal end of the biceps and then passed through a passageway drilled through the radius and then lockingly engaged through the locking apertures formed through the suture tissue restraint 67'. The free end of the suture 80 may be then passed back through the passageway and through the distal biceps and tensioned in the direction of the arrow to re-secure the biceps for healing.

Reattachment of the fibula in an ankle syndesmodic disruption is shown in FIG. 17. The suture 10 is passed through a drilled transverse passageway adjacent the end of the tibia. A mid portion of the suture 10 is lockingly engaged through the locking apertures of the suture tissue restraint 66 pressed against the tibia. Another suture tissue restraint 67 then receives both ends of the suture 10 after being passed through the lower end of the fibula and tensioned in the direction of the arrows to secure the repair.

Reattachment of the proximal biceps tendon is shown in FIG. 18 wherein a modified suture 80 absent protuberances along a mid portion thereof is wrapped around the proximal biceps tendon and there secured. The protuberance-carrying ends of the suture 80 are passed through the locking passageways of two spaced apart tissue anchors 41, each of which have been previously surgically anchored into the humeral head. The ends of the suture 80 are then tensioned in the direction of the arrows to secure the repair.

In FIGS. 19 and 20, a disc-shaped suture loop lock 106 is provided with spaced apart locking apertures 108 to secure the crisscrossed ends of each suture 10 which is initially passed around the tear formed through the capsule around a shoulder socket. This repair is notably accomplished without the typical tissue anchors, relying upon the tension locking features of each of the suture loop locks 106 as shown in FIG. 20.

FIGS. 21, 22 and 23 show alternate repair techniques utilizing the invention to repair a tear in the shoulder labrum. FIG. 21 provides a total of three separate segments of suture 10 passing therethrough while in FIG. 22, only two separate lengths of sutures 10 are provided. However, in FIG. 23 a total of four segments of two sutures 10 more tightly draw the tear together for repair.

Repair of a detached coracoclavicular ligament is shown in FIG. 24 which utilizes two separate sutures 10 each passing through drilled passageways formed through the clavicle and the coracoid as shown. The ends of each of the suture 10 are secured through modified suture tissue restraints 56' as previously described. Tensioning of all four ends of the sutures 10 provide for both strength and refined tension adjustment of the repair.

In FIGS. 25 and 26, the repair of a subscapularis detachment is there shown wherein two sutures 10 each pass through a passageway formed through the humeral head with modified suture tissue restraints 56' restraining each end of each of the sutures 10 as previously described.

The attachment of a torn rotator cuff tendon is shown in FIG. 27 utilizing a single suture row technique. The suture 10 is passed at each end thereof through the locking apertures of each tissue anchor 40 which have been previously secured into the ends of the humerus. The suture 10 is then previously passed through the rotator cuff tendon and tensioned at each end thereof in the direction of the arrows. In FIGS. 28 and 29, a double row repair of the rotator cuff tendon is there shown where two parallel sutures 10 are each passed through tissue anchors 40 and through the rotator cuff tendon as shown. In FIG. 29, an additional locking and retaining function against the rotator cuff tendon is provided by a modified suture tissue restraint 56'.

Meniscus repair is demonstrated by the use of the invention in FIGS. 30 and 31. In FIG. 30, the meniscal tear is longer requiring a total of four suture segments therethrough using two separate sutures 10. One of the sutures 10 is passed three times through the tear and anchored at a mid-portion thereof through suture tissue restraint 66 and permanently at one end thereof within suture tissue restraint 56. The permanently secured suture 10 of the suture tissue restraint 56 is then passed through the repair, exiting the opposite surface of the meniscus as shown.

In FIGS. 32 and 33, an alternate technique for meniscal tear repair is there shown wherein, in FIG. 32, a single suture 10 is passed three times through the tear utilizing the suture tissue restraints 66 and 56' as shown. In FIG. 33, a total of four passes through the tear is provided wherein the free ends of the suture 10 are drawn from the torn meniscus without the need for suture restraint.

Referring now to FIG. 34, reversal of locking protuberances and apertures is there demonstrated to be within the broad scope of this invention. Flexible elongated suture 110 is shown lockingly engaged for one-directional movement only within a pair of closely spaced locking apertures 122 of a suture tissue restraint 112. The suture has a series of spaced locking grooves formed therein which have a locking edge 116 and a ramped edge 118. Each of these grooves 114 are matingly engageable with radially inwardly extending protuberances 124 each having a square locking edge 126 and a ramped edge 128 to accomplish unidirectional movement of the suture 110.

Referring now to FIGS. 35 to 47, a number of alternate embodiments of the tissue anchor are there shown. In FIG. 35, this tissue anchor 130 is formed thereof having a solid tapered spiral thread 132 with a tissue-penetrating tip 136 at the distal end. A solid tapered head 134 includes a coaxial driving socket 138 at the proximal end of this tissue anchor 130. The head 134 also includes two intersecting suture entry and exit cavities 142 and 144 having a suture restriction 140 therebetween to insure that, once a suture is pulled through these cavities 142 and 144, it may not be removed by pulling in the opposite direction.

In FIG. 36, another tissue anchor 150 includes a solid head 154 and a hollow tapered spiral coil 152 extending therefrom. This coil 152 is formed of surgical stainless steel wire, spiral wound and having a sharpened tissue-penetrating tip 156 at the distal end thereof. Being hollow, less tissue is displaced as the spiral coil 152 is driven into tissue, particularly bone and tendons. Intersecting suture entry and exit cavities 162 and 164, separated by a suture one-way restriction 160, function as previously described in FIG. 35 for one-way insertion of a suture in accordance with this teaching.

FIG. 37 discloses yet another tissue anchor 170 having a hollow cylindrically wound spiral coil 172 formed of surgical steel wire with a sharpened tissue penetrating tip 176 at its distal end. The head 174 includes an axially aligned driving socket 178 and intersecting suture entry and exit cavities 182 and 184 with a one way restriction 180 therebetween.

Another tissue anchor 190 is shown in FIG. 38 having a hollow tapered spiral coil 192 again with a tissue penetrating tip 196 at its distal end. The opposite end of the tapered spiral coil 192 is anchored into head 194 having a coaxial driving socket 198 at its proximal end. Suture entry and exit cavities 202 and 204 are separated within the head 194 by a suture one way restriction 200. As best seen in FIG. 39, the outer edge 208 of the tapered spiral coil 192 is sharpened for enhanced tissue cutting and securement of the spiral coil 192 as its is driven into both soft and hard tissue for enhanced permanent anchoring thereof within the tissue.

As seen in FIG. 39A, one form of outer edge enhancement is in the form of a serrated edge 208a. In FIG. 40, several alternate embodiments of the cross section of the spiral coil 192b,c,d,e,f,g,h include tissue cutting outer edges at 208b,c,d,e,f,g.

Figure 41:
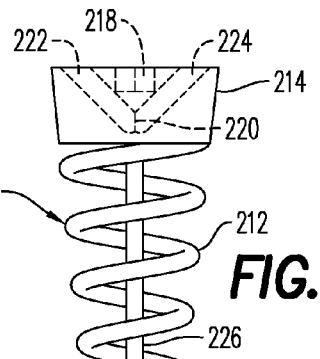
Figures 42, 43, 44:
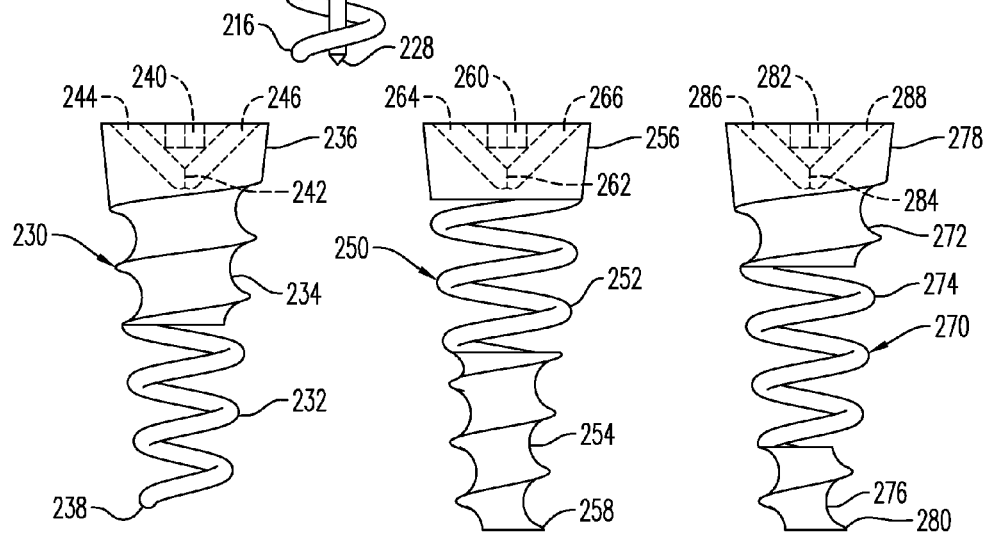
Figures 45, 46, 47:
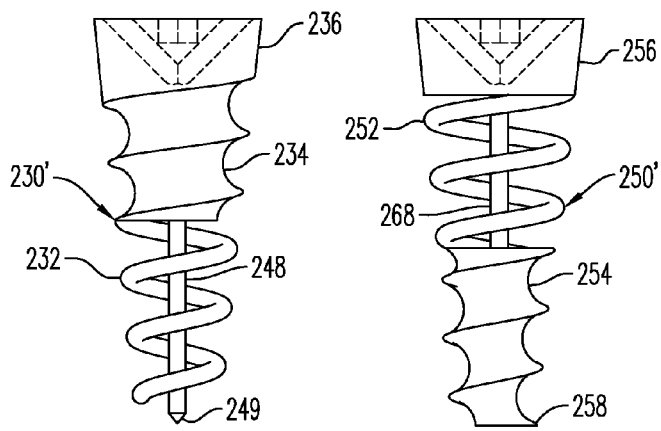
Figures 48, 49, 50, 51:
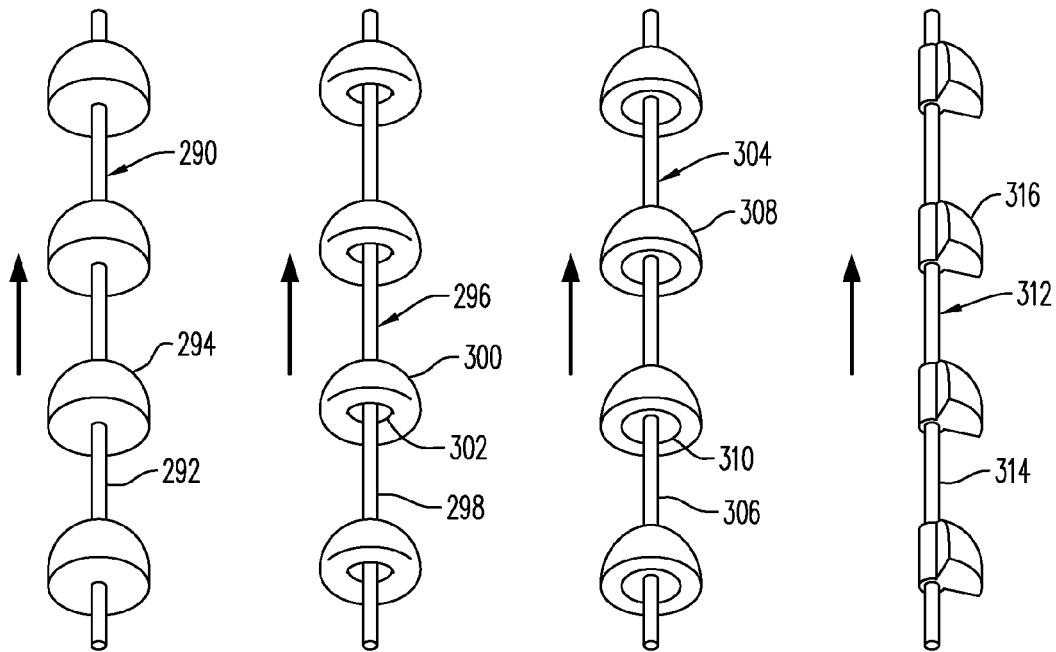

In FIG. 41, another tissue anchor is shown at 210 also having a hollow tapered spiral coil 212 with a sharpened distal tissue-penetrating tip 216. The opposite end of the coil 212 is secured into the solid head 214. Also secured within the head 214 is a coaxial cylindrical centering shaft 226 having a sharpened tip 228 which serves to center the tissue anchor 210 as it is being rotationally driven into tissue by a suitable power unit engaged into driving socket 218. Once anchored into the tissue, a suture is passed through the intersecting suture entry and exit cavities 222 and 224, the suture being permitted only one way movement therethrough by a suture one way restriction 220 therebetween.

Additional embodiments of the tissue anchor shown in FIGS. 42 to 47 generally at 230, 250, 270, 230', 250', and 270' all include combinations of tapered tissue penetrating segments in the form of tapered spiral coils 232, 252 and 274 and solid tapered screw segments 234, 254 and 276. Each suture embodiment also includes a distal tissue penetrating tip 238, 258 or 280. Each of the solid heads 236, 256 and 278 have a driving socket 240, 260 and 282 which coaxially extend from the proximal end thereof. Intersecting suture entry and exit cavity pairs 244/246, 264/266 and 286/288 are each separated for only one way suture movement therethrough by suture one way restrictions 242, 262 and 284, respectively, as previously described. The embodiments 230', 250' and 270' in FIGS. 45, 46 and 47 also include coaxially aligned centering shafts 248, 268, and 289. Centering shaft has a pointed distal tip 249 which serves to center the tissue anchor 230' during driven rotation into tissue. Centering shafts 269 and 289 are present for stabilization and added strength between the head 256 and 278 and the screw segments 254 and 276.

Figure 52:
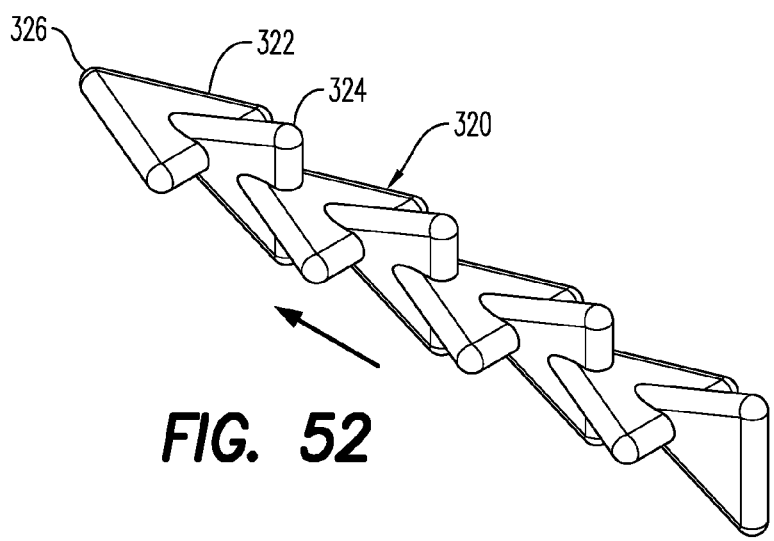

A variety of exemplary additional embodiments of the suture are shown in FIGS. 48 to 52 at 290, 296, 304, 312 and 320. Each of these suture embodiments are configured for only one way movement through appropriately configured capture arrangements formed in one or more suture tissue restraints, tissue anchors and virtually all other medical implants and devices requiring permanent securement within human tissue or bone. Each of these sutures includes an elongated flexible suture strand 292, 298, 306 and 314. Each of these sutures also includes longitudinally spaced, enlarged-in-diameter segments or protuberances 294, 300, 308, 316 and 322/324. Protuberances 294 are domed shaped, protuberances 300 are mushroom shaped having a cavity 302 formed immediately adjacent the suture strand 298, protuberances 308 are cupped-shaped also having an enlarged cavity 310 extending inwardly from the locking surface, while protuberances 316 extend around only ¼ of the circumference of the entire strand 314 demonstrating that protuberance may be nonsymmetrical. In FIG. 52 this suture 320, absent a literal suture strand, includes spaced 90° offset or staggered arrow-shaped protuberances 322 and 324. A lead-in tip 326 facilitates insertion of the lead arrow 322 into tissue or the appropriately configured one-direction capture arrangement associated with various configurations of suture tissue restraints, tissue anchors and various other surgical implants and medical devices in accordance with the teaching of this disclosure.

Referring now to FIGS. 53 to 57, another uniquely configured suture tissue restraint is shown generally at 330. This tissue restraint 330 provides finer suture tension adjustability than may be available by simply tensioning the free end of the suture to the next available protuberance within other non-adjustable tissue suture restraints. This tissue suture restraint 330 includes a disk-shaped body 332. The non-tissue contacting surface is generally concaved toward the central suture passage aperture 336, which is sized for free suture movement therethrough. A plurality of radial slots 338, 346 and 354 extend from the suture passage aperture 336, each being sized in width for the suture strand to freely pass therealong. The suture strand is then moved along through concentric slots 340, 348 or 356 into alignment with one of the selected suture strand apertures 344, 352 or 360. As best seen in FIG. 53A, the exemplary suture 10 may then be position so that one of its protuberances nests into a selected suture socket 342, 350 or 358.

As best seen in FIGS. 55, 56 and 57, each of these suture sockets 342, 350 and 358 are spaced from the tissue contact surface a different distance Ta, Tb and Tc which affords a much finer gradation of suture tensioning capability than normally afforded by simply pulling the suture to the next available protuberance along the length of the suture strand.

An alternate embodiment of this form of adjustable suture tissue restraint is shown in FIG. 58 at 370. This suture tissue restraint 370 includes a disk-shaped body 372 having a centrally positioned suture passage aperture 374 sized for free suture passage therethrough. However, only a single radial slot 380 is included which facilitates moving the suture strand of the suture therealong into concentric slot 382 and into alignment with suture strand aperture 378 or further along concentric slot 388 into alignment with suture strand 386 or still further along concentric slot 394 into suture strand aperture 392. The appropriate protuberance is then nestled securely into the corresponding suture socket 376, 384 or 390 in a manner similar to that shown in FIG. 53A.

Referring now to FIGS. 59 to 64, an expandable suture tissue restraint is there shown at numeral 400. This concept incorporates circumferential expandability in direction of the arrow in FIG. 59 to accommodate one-way passage of each suture protuberance through the expandable suture-locking aperture 404. This restraint 400 includes a plurality of circumferentially spaced solid segments 402 spaced apart by a series of expandable aperture segments 406. The inward tapered surfaces of these segments 402 and 406 define the tapered walls of a locking aperture 404.

Each expandable aperture segment 406 includes alternating resilient layers 418 and solid layers 419 bonded together and to the ends of the corresponding solid segments 402. As a suture 410 shown in FIG. 62 having tapered truncated conical-shaped spaced saw tooth-shaped protrusions 412 is drawn through the suture locking aperture 404, the circumference of the locking aperture 404 expands in the direction of arrows 59 best seen in FIGS. 63 and 64 to allow the suture 410 to be pulled therethrough only in the direction of the arrow in FIG. 62, surfaces 416 and 418 interacting to prevent reverse movement of the suture 410.

Referring additionally to FIGS. 63 and 64, alternate configurations of the protuberance 22 and 34, respectively, will also be lockingly passable in one way fashion in the direction of the arrow causing the expansion of the resilient segments 418 as the corresponding protuberance 22 or 34 passes forcibly therethrough.

In FIGS. 65 and 66, an alternate embodiment to that shown in FIG. 59 is shown generally at numeral 400' which includes substantially the same elements of embodiment 400 except for the addition of an elastic resilient O-ring 420 tightly fitted into an annular grove 422 formed inwardly into each of the solid segments 402'. The O-ring 420 has a relaxed diameter smaller than that of the annular grove 422 such that, when stretched into place within the annular grove 422, resistance to elastically stretching the diameter of the suture-locking aperture 404 is increased.

In FIGS. 67 to 73, two embodiments of a pie-shaped expandable suture tissue restraint are there shown at 430 and 430a. These embodiments, 430 and 430a, have a generally button or disk shaped body 432 and are preferably compatible with sutures having a spherical protuberance as described above and include a plurality of spaced apart rigid sectors 434 which are separated by very thin and thus resilient flat disk 436 as best seen in FIG. 70B. Alternately, this resilient flat disk 436 may be formed of a more resilient elastomeric material. The expandable suture-locking aperture 438 is configured having cylindrical aperture segments 440 and outwardly tapered inlet aperture segments 432 configured to allow a spherical protuberance or the like of a suture to pass downwardly therethrough in the direction of the arrow in FIGS. 70A and 70B by the elastic expansion of suture-locking aperture 438. The outlet aperture segments 444 seat the spherical protuberance but will not allow it to pass back through the suture-locking aperture 438, thus locking the suture in place relative to the expandable suture restraint 430.

Referring additionally to FIGS. 71 and 72, an alternate embodiment to that shown in FIG. 67 is there shown at 430a which includes a disk-shaped body 432a having spaced apart rigid sectors 434a held together by thinner resilient disk 436 as previously described. A resilient O-ring 450 is stretchingly embedded into an annular groove 452 formed into the outer ends of each of the rigid sectors 434a for enhanced elasticity of the expandable suture locking aperture 438 as previously described.

Referring now to FIGS. 74 and 75, another alternate embodiment of the expandable suture restraint of FIG. 67 is there shown generally at numeral 430b. In this embodiment 430b, one of the rigid sectors 434b is deleted as shown at 454. All other features of this embodiment 430b are as described with respect to FIG. 71. This disk-shaped body thus acts as a C-shaped body and is free to elastically expand in the direction of the arrows to allow resilient enlargement of locking aperture 438 to 438' when a protuberance is forcibly urged therethrough only in the direction of the arrow.

Referring now to FIGS. 76 and 76A, two additional alternative embodiments of the expandable suture tissue restraint of FIG. 1 are there shown generally at numerals 430c and 430d. Each of these embodiments 430c and 430d provide tapered segments 456 and 456a of each rigid sector 434c and 434d, respectively, which collectively define a centered extension of the tissue contact surfaces 458 and 458a which serve to better avoid lateral movement of the suture tissue restraint 430c and 430d when embedded into soft tissue as the suture is tensioned.

Referring now to FIGS. 77 to 82, a series of suture/tissue restraint arrangements 460, 480, 500, 520, 540, and 560 including sutures 462, 482, 502, 522, 542 and 562 inserted into suture tissue restraints 472, 492, 512, 532, 550 and 572 are there shown. In these arrangements, the protuberances 464, 484, 502, 524, 544 and 564 which are attached to or formed as a part of the corresponding suture strand 466, 486, 506, 526, 546 and 566 resiliently deform as they are pulled through the respective suture apertures 474, 492, 514, 536, 552 and 574 in the direction of the corresponding arrows. The protuberances are resiliently deformed by the displacing interaction of the surfaces 468/476, 488/494, 508/516, 528/534, 548/554, and 568/576. Locking resistance to reverse direction movement of each of these sutures is achieved by the overall configuration of each of the protuberances and the mating configurations of surfaces 470/478, 498/496, 510/518, 530/538, 556/558, and 570/578.

Referring lastly to FIGS. 83 and 84, another embodiment of the tissue anchor is there shown at numeral 580. This exemplary embodiment 580 includes a solid tapered spiral thread 582 having a distal tissue penetrating tip 584 and a tapered head 586 formed having an axially aligned driving socket 594 formed into the proximal end of the tissue anchor 580. This embodiment 580 utilizes the resilient protuberance concept previously described in FIGS. 77 to 82, wherein the suture passage 588 is arcuately configured for smooth passage of the resiliently collapsed protuberances 464' as they are forced against the head deforming inlet surface 590 as the suture is pulled in the direction of the arrow. Reverse movement of the suture is prohibited by the interaction of surface 470 of the backside of each protuberance 464 against the head locking surface 492.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. A surgical tissue engaging member for tissue repair and reattachment of torn tissue to a tissue substrate, medical prosthesis, or medical implant in conjunction with an elongated slender flexible suture member having a plurality of longitudinally spaced protuberances along a length thereof, said tissue engaging member comprising:
   an expandable suture tissue restraint comprising a plurality of circumferentially spaced solid segments;
   a series of expandable aperture segments each having a first and a second end secured to adjacent solid segments with said solid segments and expandable aperture segments defining an expandable locking aperture;
   said solid segments and said expandable aperture segments having inward tapered surfaces defining an inward tapered wall at a circumference of said expandable locking aperture; and
   said expandable suture tissue restraint being circumferentially expandable for enabling the plurality of longitudinally spaced protuberances of the flexible suture member to pass along said inward tapered surfaces of said expandable locking aperture in only one direction through said expandable locking aperture.

2. The surgical tissue engaging member as set forth in claim 1, wherein each of said plurality of spaced solid segments has a generally triangular shape.

3. The surgical tissue engaging member as set forth in claim 1, wherein said plurality of spaced solid segments are alternately spaced between said expandable aperture segments.

4. The surgical tissue engaging member as set forth in claim 1, wherein each of the plurality of longitudinally spaced protuberances along the length of said elongated slender flexible suture comprises tapered truncated conical-shaped spaced saw tooth-shaped protrusions.

5. The surgical tissue engaging member as set forth in claim 1, wherein each of the plurality of longitudinally spaced protuberances along the length a of said elongated slender flexible suture comprises generally spherical-shaped protrusions.

6. The surgical tissue engaging member as set forth in claim 1, including an annular grove formed inwardly into each of said solid segments about a outer periphery thereof; and
    an elastic resilient O-ring having a relaxed diameter smaller than said annular groove;
    said elastic resilient O-ring being tightly fitted into said annular groove to increase the resistance to elastic stretching of said expandable locking aperture.

7. The surgical tissue engaging member for tissue repair and reattachment of torn tissue to a tissue substrate, medical prosthesis, or medical implant in conjuction with an elongated slender flexible suture member having a plurality of longitudinally spaced protuberances along a length thereof, said tissue engaging member comprising:
    an expandable suture tissue restraint comprising a plurality of circumferentially spaced solid segments;
    a series of expandable aperture segments each having a first and a second end secured to adjacent solid segments with said solid segments and expandable aperture segments defining an expandable locking aperture;
    said solid segments and said expandable aperture segments having inward tapered surfaces defining an inward tapered wall at a circumference of said expandable locking aperture;
    said expandable suture tissue restraint being circumferentially expandable for enabling the plurality of longitudinally space protuberances of the flexible suture member to pass along said inward tapered surfaces of said expandable locking aperture in only one direction through said expandable locking aperture; and
    each of said expandable aperture segments being resilient.

8. The surgical tissue engaging member for tissue repair and reattachment of torn tissue to a tissue substrate, medical prosthesis, or medical implant in conjunction with an elongated slender flexible suture member having a plurality of longitudinally spaced protuberances along a length thereof, said tissue engaging member comprising:
    an expandable suture tissue restraint comprising a plurality of circumferentially spaced solid segments spaced apart by a series of expandable aperture segments defining an expandable locking aperture;
    said solid segments and expandable aperture segments defining inward tapered surfaces forming a tapered wall at a circumference of said expandable locking aperture;
    said expandable suture tissue restraint being circumferentially expandable for enabling the plurality of longitudinally spaced protuberances of the flexible suture member to pass along said inward tapered surfaces of said expandable locking aperture in only one direction through said expandable locking apertures;
    each of said expandable aperture segments includes alternating resilient layers and solid layers secured together between a first and a second end of each of said expandable aperture segments; and
    said first and second ends of each of said expandable aperture segments being secured to adjacent solid segments.

9. A surgical tissue engaging member for tissue repair and reattachment of torn tissue to a tissue substrate, medical prosthesis, or medical implant in conjunction with an elongated slender flexible suture member having a plurality of longitudinally spaced protuberances along a length thereof, said tissue engaging member comprising:
    an expandable suture tissue restraint comprising a plurality of solid segments with circumferentially spacings therebetween;
    a series of expandable aperture segments each having a first and a second end;
    each of said expandable aperture segments located in said spacings between said plurality of solid segments for securing adjacent solid segments with said solid segments and expandable aperture segments defining an expandable locking aperture;
    said solid segments and said expandable aperture segments having inward tapered surfaces defining an inward tapered wall at a circumference of said expandable locking aperture; and
    said expandable suture tissue restraint being expandable for enabling the plurality of a longitudinally spaced protuberances of the flexible suture member to pass along said inward tapered surfaces of said expandable locking aperture in only one direction through said expandable locking apertures.

\* \* \* \* \*